(12) United States Patent
Linney et al.

(10) Patent No.: US 7,105,558 B2
(45) Date of Patent: Sep. 12, 2006

(54) GASTRIN AND CHOLECYSTOKININ RECEPTOR LIGNADS (IV)

(75) Inventors: Ian Duncan Linney, London (GB); Iain Mair McDonald, London (GB)

(73) Assignee: The James Black Foundation Limited, London (GB)

(*) Notice: Subject to any disclaimer, the term of this patent is extended or adjusted under 35 U.S.C. 154(b) by 269 days.

(21) Appl. No.: 10/275,615

(22) PCT Filed: May 4, 2001

(86) PCT No.: PCT/GB01/01987

§ 371 (c)(1),
(2), (4) Date: Nov. 7, 2002

(87) PCT Pub. No.: WO01/85704

PCT Pub. Date: Nov. 15, 2001

(65) Prior Publication Data

US 2003/0195237 A1 Oct. 16, 2003

(30) Foreign Application Priority Data

May 8, 2000 (GB) .......................... 0011094.0

(51) Int. Cl.
A61K 31/4192 (2006.01)
C07D 249/06 (2006.01)
A61P 1/04 (2006.01)

(52) U.S. Cl. ........................ 514/383; 548/250
(58) Field of Classification Search ............. 548/250
See application file for complete search history.

(56) References Cited

FOREIGN PATENT DOCUMENTS

WO  WO 95/30647  11/1995
WO  WO 00/27823  5/2000

OTHER PUBLICATIONS

Chemical Abstracts, vol. 80, No. 7, Feb. 18, 1974, Columbus, Ohio: Belikov et al., "Phenylhydrazones of alpha–keto acids.", XP002172262.
Abdel–Fattach et al., "A New Route For the Synthesis of Fused Triazoles" Indian J. Chem. Sect. B. (1983), 22B(2) 125–7, XP001007419.
Settimo et al., "1,2,3–Triazole Derivatives of Salicylic Acid", Farmaco, Ed. Sci. (1983), 38(10), 725–37, XP001007418.

*Primary Examiner*—Kamal A. Saeed
(74) *Attorney, Agent, or Firm*—Heller Ehrman LLP

(57) ABSTRACT

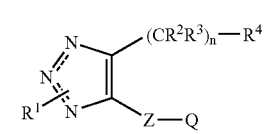 (I)

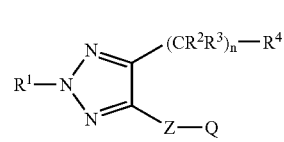

(II)

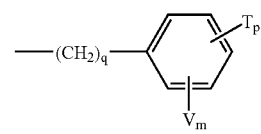

(a)

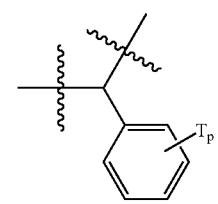

(b)

Compounds of the formula (I) or (II) and their pharmaceutically acceptable salts are ligands at gastrin and/or cholecystokinin receptors n is from 1 to 4; $R^4$ is $C_1$ to $C_{15}$ hydrocarbyl wherein up to two C atoms may optionally be replaced by N, O and/or S atoms and up to three H atoms may optionally be replaced by halogen atoms; Z is —$(NR^5)_a$—CO—$(NR^6)_b$-(wherein a is 0 or 1, b is 0 or 1, and $R^5$ and $R^6$ are independently selected from H, Me, Et, Pr, Bn), —CO—$NR^5$—$CH_2$—CO—$NR^6$—, —CO—O—, —$CH_2$—$CH_2$—, —CH=CH—, $CH_2$—$NR^6$— or a bond; Q is $R^7$V, or(a) wherein $R^7$ is —$CH_2$—; —$CH_2$—; or(b) $R^7$ and $R^6$, together with the nitrogen atom to which $R^6$ is attached, form a piperidine or pyrrolidine ring which is substituted by V; V is —CO—NH—$SO_2$-Ph, —$SO_2$—NH—CO-Ph, $CH_2OH$, or a group of the formula —$R^8U$, (wherein U is —COOH, tetrazolyl, —CONHOH— or —$SO_3H$; and $R^8$ is a bond; $C_1$ to $C_6$ hydrocarbylene, optionally substituted by hydroxy, amino or acetamino; —O—$(C_1$ to $C_3$ alkylene)-; —$SO_2NR^9$—$CHR^{10}$—; —CO—$NR^9$—$CHR^{10}$—, $R^9$ and $R^{10}$ being independently selected from H and methyl; or —NH—$(CO)_c$—$CH_2$—, c being 0 or 1); m is 1 or 2; q is from 0 to 2, with the proviso that q is 1 or 2 when Z is a bond); Compositions comprising a compound of formula (I) or (II) are also described.

31 Claims, No Drawings

GASTRIN AND CHOLECYSTOKININ RECEPTOR LIGNADS (IV)

This application is the national phase under 35 U.S.C. § 371 of PCT International Application No. PCT/GB01/01987 which has an International filing date of May 4, 2001, the disclosure of which is incorporated herein by reference in its entirety.

This invention relates to gastrin and cholecystokinin (CCK) receptor ligands. (The receptor previously known as the $CCK_B$/gastrin receptor is now termed the $CCK_2$ receptor). The invention also relates to methods for preparing such ligands and to compounds which are useful intermediates in such methods. The invention further relates to pharmaceutical compositions comprising such ligands and methods for preparing such pharmaceutical compositions.

Gastrin and the cholecystokinins are structurally related neuropeptides which exist in gastrointestinal tissue and the central nervous system (Mutt V., *Gastrointestinal Hormones*, Glass G. B. J., ed., Raven Press, New York, p. 169; Nisson G., ibid., p. 127).

Gastrin is one of the three primary stimulants of gastric acid secretion. Several forms of gastrin are found including 34-, 17- and 14-amino acid species with the minimum active fragment being the C-terminal tetrapeptide (TrpMetAspPhe-$NH_2$) which is reported in the literature to have full pharmacological activity (Tracey H. J. and Gregory R. A., *Nature* (London), 1964, 204, 935). Much effort has been devoted to the synthesis of analogues of this tetrapeptide (and the N-protected derivative Boc-TrpMetAspPhe-$NH_2$) in an attempt to elucidate the relationship between structure and activity.

Natural cholecystokinin is a 33 amino acid peptide (CCK-33), the C-terminal 5 amino acids of which are identical to those of gastrin. Also found naturally is the C-terminal octapeptide (CCK-8) of CCK-33.

The cholecystokinins are reported to be important in the regulation of appetite. They stimulate intestinal mobility, gall bladder contraction, pancreatic enzyme secretion and are known to have a trophic action on the pancreas. They also inhibit gastric emptying and have various effects in the central nervous system.

Compounds which bind to cholecystokinin and/or gastrin receptors are important because of their potential pharmaceutical use as antagonists or partial agonists of the natural peptides.

A number of gastrin antagonists have been proposed for various therapeutic applications, including the prevention of gastrin-related disorders, gastrointestinal ulcers, Zollinger-Ellison syndrome, antral G cell hyperplasia and other conditions in which lower gastrin activity or lower acid secretion is desirable. The hormone has also been shown to have a trophic action on cells and so an antagonist may be expected to be useful in the treatment of cancers, particularly in the stomach and the colon.

Possible therapeutic uses for cholecystokinin antagonists include the control of appetite disorders such as anorexia nervosa and the treatment of pancreatic inflammation, biliary tract disease and various psychiatric disorders. Other possible uses are in the potentiation of opiate (for example morphine) analgesia and in the treatment of cancers, especially of the pancreas. Moreover, ligands for cholecystokinin receptors in the brain (so-called $CCK_2$ receptors) have been claimed to possess anxiolytic activity.

PCT/GB99/03733 describes a class of compounds having gastrin antagonist activity. This class of compounds is typically characterised by a 5-membered ring, preferably an imidazole or pyrrole, having two hydrocarbyl substituents and an amide or urea-type substituent.

According to the present invention, there are provided compounds of formula (I) or (II)

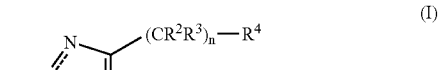

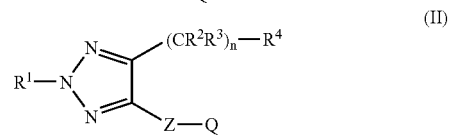

wherein n is from 1 to 4;

$R^1$ is H or $C_1$ to $C_{15}$ hydrocarbyl wherein up to three C atoms may optionally be replaced by N, O and/or S atoms and up to three H atoms may optionally be replaced by halogen atoms;

$R^2$ is selected from H, Me, Et, Pr and OH, each $R^2$ being independently selected from H, Me, Et, Pr and OH when n is greater than 1;

$R^3$ (when n is 1) is selected from H, Me, Et and Pr; or (when n is greater than 1) each $R^3$ is independently selected from H, Me, Et and Pr, or two $R^3$ groups on neighbouring carbon atoms are linked to form a $C_3$ to $C_6$ carbocyclic ring, or two $R^3$ groups are absent from neighbouring carbon atoms which are linked by a double bond; or $R^2$ and $R^3$ on the same carbon atom together represent an =O group;

$R^4$ is $C_1$ to $C_{15}$ hydrocarbyl wherein up to two C atoms may optionally be replaced by N, O and/or S atoms and up to three H atoms may optionally be replaced by halogen atoms;

Z is —$(NR^5)_a$—CO—$(NR^6)_b$— (wherein a is 0 or 1, b is 0 or 1, and $R^5$ and $R^6$ are independently selected from H, Me, Et Pr, Bn), —CO—$NR^5$—$CH_2$—CO—$NR^6$—, —CO—O—, —$CH_2$—$CH_2$—, —CH=CH—, —$CH_2$—$NR^6$— or a bond;

Q is —$R^7V$, or

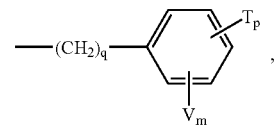

(wherein $R^7$ is —$CH_2$—; —$CH_2$—$CH_2$—; or

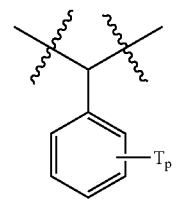

or $R^7$ and $R^6$, together with the nitrogen atom to which $R^6$ is attached, form a piperidine or pyrrolidine ring which is substituted by V;

V is —CO—NH—$SO_2$-Ph, —$SO_2$—NH—CO-Ph, —$CH_2OH$, or a group of the formula —$R^8U$, (wherein U is —COOH, tetrazolyl, —CONHOH— or —SO$_3$H; and R$^8$ is a bond; C$_1$ to C$_6$ hydrocarbylene, optionally substituted by hydroxy, amino or acetamido; —O—(C$_1$ to C$_3$ alkylene)—; —SO$_2$NR$^9$—CHR$^{10}$—; —CO—NR$^9$—CHR$^{10}$—, R$^9$ and R$^{10}$ being independently selected from H and methyl; or —NH—(CO)$_c$—CH$_2$—, c being 0 or 1);

T is C$_1$ to C$_6$ hydrocarbyl, —NR$^{11}$R$^{12}$ (wherein R$^{11}$ and R$^{12}$ are independently selected from H, Me, Et, Pr, Bn), —OME, —OH, —CH$_2$OH, halogen or trihalomethyl;

m is 1 or 2;

p is from 0 to 3; and q is from 0 to 2, with the proviso that q is 1 or 2 when Z is a bond);

or a pharmaceutically acceptable salt thereof.

In certain compounds according to the invention, Z is —(NR$^5$)$_a$—CO—(NR$^6$)$_b$—, —CO—NH—CH$_2$—CO—NH— or a bond; Q is

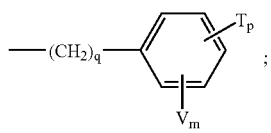

V is —CO—NH—SO$_2$-Ph, —SO$_2$—NH—CO-Ph, —OCH$_2$COOH, tetrazolyl or —(CH$_2$)$_s$COOH, wherein s is from 0 to 2; and T is C$_1$ to C$_6$ hydrocarbyl, —NR$^{11}$R$^{12}$, —OMe, —OH, CH$_2$—OH or halogen.

A further group of compounds according to the invention are those in which Z is —(NR$^7$)$_a$—CO—(NR$^6$)$_b$—, Q is —(CH$_2$)$_r$COOH, wherein r is from 1 to 3; and T is C$_1$ to C$_6$ hydrocarbyl, —NR$^{11}$R$^{12}$, —OMe, —OH, —CH$_2$OH or halogen.

A still further group of compounds according to the invention are those in which -Z-Q is

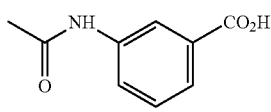

Preferably R$^1$ is C$_1$ to C$_{12}$ hydrocarbyl wherein one C atom may optionally be replaced by N or O and up to three H atoms may optionally be replaced by F, Cl or Br. More preferably R$^1$ is C$_3$ to C$_{10}$ alicyclic; phenyl, pyridyl, phenyl C$_1$–C$_3$ alkyl or pyridyl C$_1$–C$_3$ alkyl (all optionally substituted with OMe, NMe$_2$, CF$_3$, Me, F, Cl, Br or I); or C$_1$ to C$_8$ alkyl. Alicyclic groups include C$_5$ to C$_8$ cycloalkyl, C$_7$ to C$_{10}$ polycycloalkyl, C$_5$ to C$_8$ cycloalkenyl and C$_7$ to C$_{10}$ polycycloalkenyl, all optionally substituted with methyl. Phenyl C$_1$–C$_3$ alkyl includes, for example, benzyl.

Most preferably R$^1$ is cyclohexyl.

Preferably R$^2$ is H, R$^3$ is H and n is 1, 2 or 3.

In certain compounds according to this invention R$^4$ is C$_3$ to C$_{15}$ carbocyclic, optionally substituted with 1, 2 or 3 halogen atoms. In other compounds according to this invention, R$^4$ is —NH—R$^{13}$ or —OR$^{13}$, wherein R$^{13}$ is C$_3$ to C$_{12}$ carbocyclic, optionally substituted with 1, 2 or 3 halogen atoms. Preferably R$^4$ is —O-adamantyl, —O-cycloheptyl, —O-cyclohexyl or —O-phenyl. Most preferably R$^4$ is —O-adamantyl.

Preferably V is —CO—NH—SO$_2$-Ph, —SO$_2$—NH—CO-Ph, —OCH$_2$COOH, tetrazolyl or (CH$_2$)$_s$COOH, wherein s is from 0, 1 or 2. Most preferably V is CH$_2$COOH, COOH or tetrazolyl.

Preferably Z is —CO—NH—.

Preferably Q is

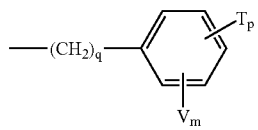

and more preferably

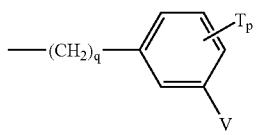

p is preferably 0 or 1, and q is preferably 0. If p is greater than 0, then T is preferably C$_1$ to C$_6$ hydrocarbyl or halo.

m is preferably 1, and V is preferably —CO$_2$H, —CH$_2$CO$_2$H or tetrazolyl.

R$^8$ is preferably a bond, C$_1$ or C$_2$ alkylene (optionally substituted by hydroxy, amino or acetamido), —O—(C$_1$ to C$_3$ alkylene)-; —SO$_2$NR$^9$CHR$^{10}$—; —CO—NR$^9$—CHR$^{10}$—, —NH—(CO)$_c$—CH$_2$—, or a group of the formula

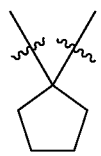

Certain compounds of the invention exist in various regioisomeric, enantiomeric, tautomeric and diastereomeric forms. It will be understood that the invention comprehends the different regioisomers, enantiomers, tautomers and diastereomers in isolations from each other as well as mixtures.

Compounds of the present invention wherein -Z-Q is

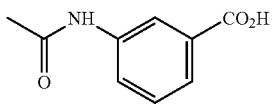

may conveniently be prepared by the route exemplified in Reaction Scheme 1.

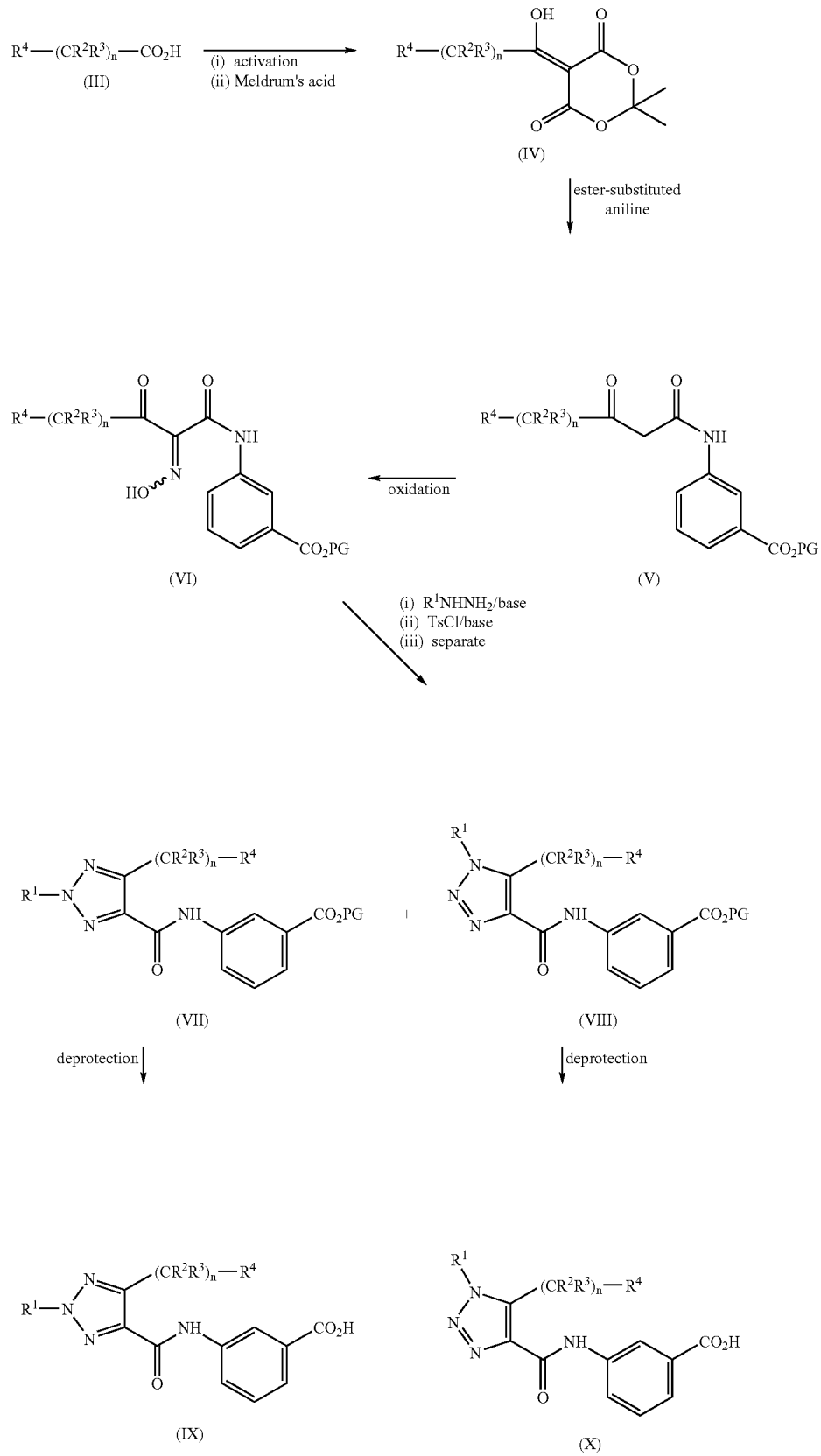
Reaction Scheme 1

Carboxylic acid (III) is activated with for example CDI and reacted with Meldrum's acid to provide enol (IV). Nucleophilic addition of a suitably protected 3-carboxyaniline furnishes β-ketoamide (V). Oxidation with for example sodium nitrite yields oxime (VI). Reaction of the keto group on compound (VI) with a suitable $R^1$—$NHNH_2$ forms an imine which cyclises to a triazole (VII) or (VIII) after activation of the hydroxyl group of the oxime.

Triazoles (VII) and (VIII) are separated (by for example silica gel chromatography) and deprotected to give the requisite carboxylic acids (IX) and (X).

Their isomers may be prepared by the route exemplified in Reaction Scheme 2.

plasma half-life. Further discussion of pro-drugs may be found in Stella, V. J. et al., "Prodrugs", *Drug Delivery Systems*, 1985, pp. 112–176, and *Drugs*, 1985, 29, pp. 455–473.

Pro-drug forms of the pharmacologically-active compounds of the invention will generally be compounds according to formula (I) or (II) having an acid group which is esterified or amidated. Included in such esterified acid groups are groups of the form —$COOR^a$, wherein $R^a$ is $C_1$ to $C_5$ alkyl, phenyl, substituted phenyl, benzyl, substituted benzyl, or one of the following:

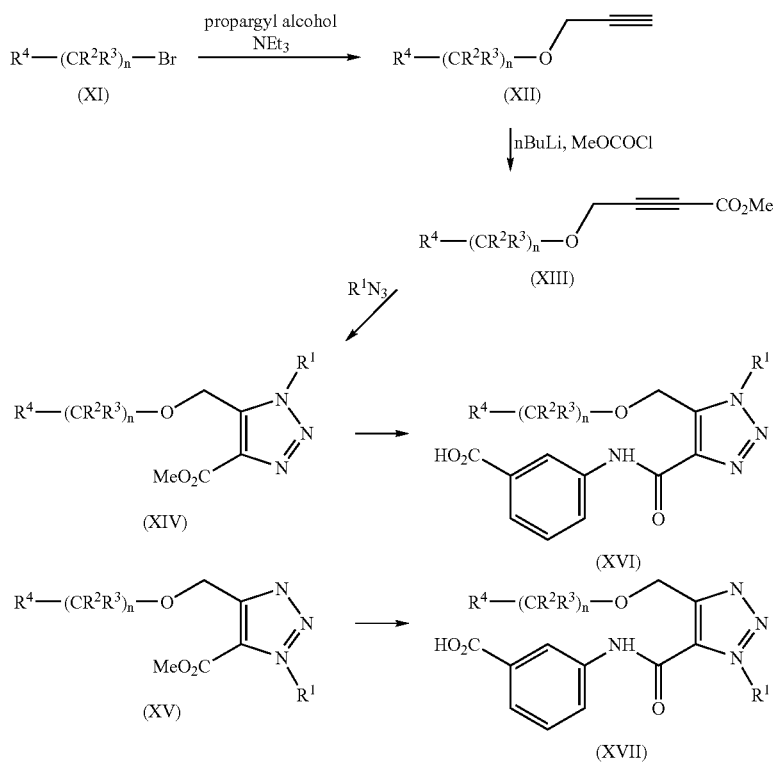

Alkyl bromide (XI) is substituted with propargyl alcohol to afford alkyne (XII). The alkyne is deprotonated and then acylated to give (XIII). The isomeric triazoles (XIV) and (XV) are produced by a 1,3 dipolar cycloaddition reaction with a suitable azide compound. The cycloaddition adducts (XIV) and (XV) are then converted to the requisite acids (XVI) and (XVII) via a hydrolysis, coupling and hydrolysis sequence.

Hence, the present invention provides methods of making compounds according to formula (I) or (II).

The invention also comprehends derivative compounds ("pro-drugs") which are degraded in vivo to yield the species of formula (I) or (II). Pro-drugs are usually (but not always) of lower potency at the target receptor than the species to which they are degraded. Pro-drugs are particularly useful when the desired species has chemical or physical properties which make its administration difficult or inefficient. For example, the desired species may be only poorly soluble, it may be poorly transported across the mucosal epithelium, or it may have an undesirably short

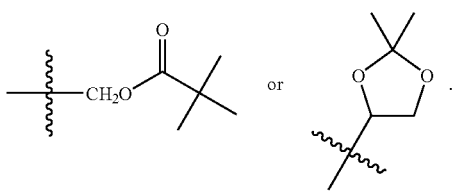

Amidated acid groups include groups of the formula $CONR^bR^c$, wherein $R^b$ is H, $C_1$ to $C_5$ alkyl, phenyl, substituted phenyl, benzyl, or substituted benzyl, and $R^c$ is —OH or one of the groups just recited for $R^b$.

Compounds of formula (I) or (II) having an amino group may be derivatised with a ketone or an aldehyde such as formaldehyde to form a Mannich base. This will hydrolyse with first order kinetics in aqueous solution.

Another aspect of the present invention is a pharmaceutical composition comprising a compound of formula (I) or (II) substantially as described herein before with a pharmaceutically acceptable diluent or carrier.

Yet another aspect of the present invention is a method of making a pharmaceutical composition comprising a compound of formula (I) or (II) substantially as described herein before, comprising mixing said compound with a pharmaceutically acceptable diluent or carrier.

Pharmaceutically acceptable salts of the acidic or basic compounds of the invention can of course be made by conventional procedures, such as by reacting the free base or acid with at least a stoichiometric amount of the desired salt-forming acid or base.

Pharmaceutically acceptable salts of the acidic compounds of the invention include salts with inorganic cations such as sodium, potassium, calcium magnesium, and zinc, and salts with organic bases. Suitable organic bases include N-methyl-D-glucamine, arginine, benzathine, diolamine, olamine, procaine and tromethamine.

Pharmaceutically acceptable salts of the basic compounds of the invention include salts derived from organic or inorganic acids. Suitable anions include acetate, adipate, besylate, bromide, camsylate, chloride, citrate, edisylate, estolate, fumarate, gluceptate, gluconate, glucuronate, hippurate, hyclate, hydrobromide, hydrochloride. iodide, isethionate, lactate, lactobionate, maleate, mesylate, methylbromide, methylsulfate, napsylate, nitrate, oleate, pamoate, phosphate, polygalacturonate, stearate, succinate, sulfate, sulfosalicylate, tannate, tartrate, terephthalate, tosylate and triethiodide.

It is anticipated that the compounds of the invention can be administered by oral or parenteral routes, including intravenous, intramuscular, intraperitoneal, subcutaneous, rectal and topical administration, and inhalation.

For oral administration, the compounds of the invention will generally be provided in the form of tablets or capsules or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate and lactose. Corn starch and alginic acid are suitable disintegrating agents. Binding agents may include starch and gelatine. The lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatine capsules in which the active ingredient is mixed with a solid diluent and soft gelatine capsules wherein the active ingredient is mixed with water or an oil such as peanut oil, liquid paraffin or olive oil.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

Effective doses of the compounds of the present invention may be ascertained by conventional methods. The specific dosage level required for any particular patient will depend on a number of factors, including severity of the condition being treated, the route of administration and the weight of the patient. In general, however, it is anticipated that the daily dose (whether administered as a single dose or as divided doses) will be in the range 0.001 to 5000 mg per day, more usually from 1 to 1000 mg per day, and most usually from 10 to 200 mg per day. Expressed as dosage per unit body weight, a typical dose will be expected to be between 0.01 µg/kg and 50 mg/kg, especially between 10 µg/kg and 10 mg/kg, eg. between 100 µg and 2 mg/kg.

In a further aspect of the present invention there are provided pharmaceutical compositions comprising a compound according to formula (I) or (II) and a proton pump inhibitor. Compositions comprising a CCK/gastrin antagonist and a proton pump inhibitor are described in International patent application WO93/12817, incorporated herein by reference.

In one aspect of the present invention the proton pump inhibitor is omeprazole which is 5-methoxy-2-[[(4-methoxy-3,5-dimethyl-2-pyridinyl)-methyl]sulfinyl]-1H-benzimidazole;

BY308;

SK & 95601 which is 2-[[(3chloro-4-morpholino-2-pyridyl) methyl]sulfinyl]-5-methoxy-(1H)-benzimidazole;

SK & 96067 which is 3-butyryl-4-(2-methylphenylamino)-8-methoxyquinoline;

5-trifluoromethyl-2-[4methoxy-3-methyl-2-pyridyl-methyl]-thio-[1H]-benzimidazole;

or pharmaceutically acceptable salts thereof.

These proton pump inhibitors are described and claimed in U.S. Pat. Nos. 4,472,409 and 4,255,431. These patents are incorporated herein by reference.

In a further aspect of the present invention, the proton pump inhibitor is lansoprazole which is 2-[[[3-methyl-4-(2,2,2-trifluoroethoxy)-2-pyridinyl]methyl]sulfinyl]-1H-benzimidazole;

pantoprazole which is 5-(difluoromethoxy)-2-[[(3,4-diethoxy-2-pyridinyl)methyl]sulfinyl]-1H-benzmidazole;

perprazole;

rabeprazole which is 2-[[4-(3-methoxypropoxy)-3-methylpyridin-2-yl]methylsulfinyl]-1H-benzimidazole;

[[4-(2,2,2-trifluoroethoxy)-3-methyl-2-pyridyl]-methyl] sulfenamide;

(Z)-5-methyl-2-[2-(1-naphthyl)ethenyl]4-piperidinopyridine HCl;

2-(4-cyclohexyloxy-5-methylpyridin-2-yl)-3-(1-naphthyl)-1-propanol;

methyl 2-cyano-3-(ethylthio)-3-(methylthio)-2propenoate;

2-((4-methoxy-2-pyridyl)methylsulphinyl)-5-(1,1,2,2-tetrafluoroethoxy)-1H-benzimidazole sodium;

2-[[[4-(2,2,3,3,4,4,4-heptafluorobutoxy)-2-pyridyl]methyl) sulfinyl]-1H-thieno[3,4-d]imidazole;

2-[[[4-(2,2,2-trifluoroethoxy)-3-methyl-2-pyridyl]methyl] sulfinyl]-1H-benzimidazole;

2-[[[4-(2,2,2-trifluoroethoxy)-3-methyl-2-pyridyl]methyl] sulfinyl]-1H-benzimidazole;

2-methyl-8-(phenylmethoxy)-imidazo(1,2-A)-pyridine-3-acetonitrile;

(2-((2-dimethylaminobenzyl)sulfinyl)-benzimidazole);

4-(N-allyl-N-methylamino)-1-ethyl-8-((5-fluoro-6-methoxy-2-benzimidazolyl)sulfinylmethyl)-1-ethyl 1,2,3,4-tetrahydroquinolone;

2-[[(2-dimethylaminophenyl)methyl]sulfinyl]-4,7-dimethoxy-1H-benz imidazole;

2-[(2-(2-pyridyl)phenyl)sulfinyl)-1H-benzimidazole;
(2-[(2-amino-4-methylbenzyl)sulfinyl]-5-methoxybenzo[d]
  imidazole;
(4(2-methylpyrrol-3-yl)-2-guanidisothiazole);
4-(4-(3-(imidazole)propoxy)phenyl)-2phenylthiazole;
(E)-2-(2-(4-(3-(dipropylamino)butoxy)phenyl)-ethenyl)
  benzoxazole;
(E)-2-(2-(4-(3-(dipropylamino)propoxy)phenyl)ethenyl)-
  benzothiazole;
Benzeneamine, 2-[[(5-methoxy-1H-benzimidazol-2-yl)
  sulfinyl]methyl)-4-methyl-;
Pumilacidin A;
2,3-dihydro-2-methoxycarbonylamino-1,2-benzisothiazol-
  3-one;
2-(2-ethylaminophenylmethylsulfinyl)-5,6-
  dimethoxybenzimidazole;
2-methyl-8-(phenylmethoxy)imidazo[1,2-a)pyridine-3-
  acetonitrile;
3-amino-2-methyl-8-phenylmethoxyimidazo[1,2-a)-
  pyrazine HCl;
2-[[(3-chloro-4-morpholino-2-pyridyl)methyl]-sulfinyl)-5-
  methoxy-(1H)-benzinidazole;
[3-butyryl-4-(2-methylphenylamino)-8-methoxy-
  quinoline);
2-indanyl 2-(2-pyridyl)-2-thiocarbamoylacetate HCl;
2,3-dihydro-2-(2-pyridinyl)-thiazolo (3,2-a)-benzimidazole;
3-cyanomethyl-2-methyl-8-(3-methyl-2-butenyloxy)-(1,2-
  a)imidazopyridine;
zinc L-carnosine;
or pharmaceutically acceptable salts thereof.

Rabeprazole is described in U.S. Pat. No. 5,045,552. Lansoprazole is described in U.S. Pat. No. 4,628,098. Pantoprazole is described in U.S. Pat. No. 4,758,579. These patents are incorporated herein by reference.

Preferably, the proton pump inhibitor is selected from (RS)-rabeprazole, (RS)-omeprazole, lansoprazole, pantoprazole, (R)-omeprazole, (S)-omeprazole, perprazole, (R)-rabeprazole, (S)-rabeprazole, or the alkaline salts thereof. The alkaline salts may be, for example, the lithium, sodium, potassium, calcium or magnesium salts.

Compositions of the present invention comprising a compound of formula (I) or (II) and a proton pump inhibitor may be administered as described above. Preferably the dose of each of the active ingredients in these compositions will be equal to or less than that which is approved or indicated in monotherapy with said active ingredient.

In another aspect of this invention, there is provided a kit comprising a compound of formula (I) or (II) and a proton pump inhibitor. The kit is useful as a combined preparation for simultaneous, separate or sequential use in the treatment of patients suffering from gastrointestinal disorders.

In yet a further aspect of the present invention there is provided a method of making a pharmaceutical composition comprising a compound of formula (I) or (II) substantially as described herein before and a proton pump inhibitor, comprising mixing said compound and said proton pump inhibitor with a pharmaceutically acceptable carrier or diluent.

The term "hydrocarbyl" is used herein to refer to monovalent groups consisting of carbon and hydrogen. Hydrocarbyl groups thus include alkyl, alkenyl and alkynyl groups (in both straight and branched chain forms), cycloalkyl (including polycycloalkyl), cycloalkenyl and aryl groups, and combinations of the foregoing, such as alkylcycloalkyl, alkylpolycycloalkyl, alkylaryl, alkenylaryl, alkynylaryl, cycloalkylaryl and cycloalkenylaryl groups.

Where reference is made to a carbon atom of a hydrocarbyl group being replaced by a N, O or S atom, what is intended is that

is replaced by

or that $CH_2$ is replaced by —O— or —S—.

A "carbocyclic" group, as the term is used herein, comprises one or more closed chains or rings, which consist entirely of carbon atoms. Carbocyclic groups thus include aromatic groups (such as phenyl, naphthyl, indanyl, fluorenyl, (1,2,3,4)-tetrahydronaphthyl, indenyl and isoindenyl, and substituted derivatives thereof), and also alicyclic groups. The term "alicyclic group" refers to a carbocyclic group which does not contain an aromatic ring, and thus includes groups such as cyclopropyl, cyclobutyl, cyclopentyl, cyclohexyl, cyclohexenyl, adamantyl, norbornyl, bicyclo[2.2.2]octyl, norbornenyl and bicyclo[2.2.2]octenyl, and also groups (such as adamantanemethyl and methylcyclohexyl) which contain both alkyl or alkenyl groups in addition to cycloalkyl or cycloalkenyl moieties.

The term "aryl" is used herein to refer to an aromatic group, such as phenyl or naphthyl, or a heteroaromatic group, such as pyridyl, pyrrolyl, or furanyl.

The term "alkyl" is used herein to refer to both straight and branched chain forms.

When reference is made herein to a substituted carbocyclic group (such as substituted phenyl) or a substituted heterocyclic group, the substituents are preferably from 1 to 3 in number and selected from $C_1$ to $C_6$ alkyl, $C_1$ to $C_6$ alkoxy, thio, $C_1$ to $C_6$ alkylthio, carboxy, carboxy($C_1$ to $C_6$)alkyl, formyl, $C_1$ to $C_6$ alkylcarbonyl, $C_1$ to $C_6$ alkylcarbonylalkoxy, nitro, trihalomethyl, hydroxy, $C_1$ to $C_6$ alkylhydroxy, hydroxy($C_1$ to $C_6$)alkyl, amino, $C_1$ to $C_6$ alkylamino, di($C_1$ to $C_6$ alkyl)amino, aminocarboxy, $C_1$ to $C_6$ alkylaminocarboxy, di($C_1$ to $C_6$ alkyl)aminocarboxy, aminocarboxy($C_1$ to $C_6$)alkyl, $C_1$ to $C_6$ alkylaminocarboxy ($C_1$ to $C_6$)aklyl, di($C_1$ to $C_6$ aklyl)aminocarboxy($C_1$ to $C_6$)alkyl, $C_1$ to $C_6$ alkylcarbonylamino, $C_5$ to $C_8$ cycloalkyl, $C_5$ to $C_8$ cycloalkyl($C_1$ to $C_6$)alkyl, $C_1$ to $C_6$ alkylcarbonyl ($C_1$ to $C_6$ alkyl)amino, aryl, aryl($C_1$ to $C_6$)alkyl, ($C_1$ to $C_6$ alkyl)aryl, halo, $C_1$ to $C_6$ alkylhalo, sulphamoyl, tetrazolyl and cyano.

Most usually, substituents will be selected from $C_1$ to $C_6$ alkyl, $C_1$ to $C_6$ alkoxy, thio, $C_1$ to $C_6$ alkylthio, carboxy, carboxy($C_1$ to $C_6$)alkyl, formyl, $C_1$ to $C_6$ alkylcarbonyl, $C_1$ to $C_6$ alkylcarbonylalkoxy, nitro, trihalomethyl, hydroxy, $C_1$ to $C_6$ alkylhydroxy, hydroxy($C_1$ to $C_6$)alkyl, amino, $C_1$ to $C_6$ alkylamino, di($C_1$ to $C_6$ alkyl)amino, aminocarboxy, $C_1$ to $C_6$ alkylaminocarboxy, di($C_1$ to $C_6$ alkyl)aminocarboxy, aminocarboxy($C_1$ to $C_6$)alkyl, $C_1$ to $C_6$ alkylaminocarboxy ($C_1$ to $C_6$)alkyl, di($C_1$ to $C_6$ alkyl)aminocarboxy($C_1$ to $C_6$)alkyl, $C_1$ to $C_6$ alkylcarbonylamino, $C_5$ to $C_8$ cycloalkyl, $C_5$ to $C_8$ cycloalkyl($C_1$ to $C_6$)alkyl, $C_1$ to $C_6$ alkylcarbonyl ($C_1$ to $C_6$ alkyl)amino, halo, $C_1$ to $C_6$ alkylhalo, sulphamoyl, tetrazolyl and cyano.

The term "halogen" is used herein to refer to any of fluorine, chlorine, bromine and iodine. Most usually, however, halogen substituents in the compounds of the invention are chlorine and fluorine substituents.

The term "suitably protected" used herein refers to the use of any suitable protecting group to protect a functional group. Such protecting groups are denoted as PG, PG$^1$, PG$^2$, PG$^3$ etc. in the Reaction Scheme illustrated above. Suitable protecting groups will be readily apparent to the skilled person and may be found in, for example, Kocienski, *Protecting Groups*, Thieme, New York, 1994. For example, in the case of hydroxyl groups, suitable protecting groups may include esters, ethers (e.g. silyl ethers or alkyl ethers) or acetals. Some specific examples of typical hydroxyl protecting groups are allyl, Aloc, benzyl, BOM, t-butyl, trityl, TBS, TBDPS, TES, TMS, TIPS, PMB, MEM, MOM, MTM, and THP. In the case of nitrogen atoms, suitable protecting groups may include Boc, Aloc, Troc, benzyl, allyl, Fmoc or silyl. In the case of carboxylic acids, suitable protecting groups may include esters (e.g. benzyl, allyl, methyl or ethyl esters).

The term "activated" used herein in connection with carboxylic acids refers to any activated derivative of a carboxylic acid. Methods of activating carboxylic acids will be known to the skilled artisan and may include activation using EDC, CDI or DCC (optionally in the presence of nucleophilic catalysts such as DMAP), conversion to an acid halide such as an acid chloride (e.g. using $SOCl_2$ or oxalyl chloride) or conversion to an activated ester (such as a phenyl or pentafluorophenyl ester).

The term "activated" used herein in connection with hydroxyl groups refers to any derivative of a hydroxyl group which is a leaving group. Methods of activating hydroxyl groups in this way will be known to the skilled artisan and may include activation using a sulfonyl halide (e.g. tosyl chloride or mesyl chloride), activation with a Lewis acid (e.g. $ZnCl_2$, $SnCl_4$, $SnCl_2$, $TiCl_4$, $AlCl_3$, $BF_3$ etc.), conversion to a halogen atom (e.g. using $SOCl_2$, $PCl_3$, $PCl_5$ etc. in the case of a chlorine atom) or conversion to an ester.

The invention is now further illustrated by means of the following Examples. All reactions were performed under an atmosphere of dry argon unless otherwise stated. Dichloromethane (DCM) was freshly distilled from calcium hydride. Anhydrous tetrahydrofuran (THF) and N,N-dimethylformamide (DMF) were used.

Synthesis of Common Intermediate 3-[4-(adamantan-1-yloxy)-2-hydroxyimino-3-oxo-butyrylamino]-benzoic acid methyl ester.

Step a. (Adamantan-1-yloxy)-acetic acid.

To a stirred, ice-cooled suspension of sodium hydride (60% dispersion in mineral oil, 39.4 g, 985 mmol) in THF (250 mL) was added dropwise a solution of 1-adamantanol (50.0 g, 328 mmol) in THF (250 mL) over a period of 30 minutes. The resultant suspension was allowed to warm to ambient temperature and stirred at this temperature for 10 minutes. The suspension was re-cooled in ice/water and a solution of chloroacetic acid (46.5 g, 492 mmol) in THF (250 mL) was added slowly over 30 minutes (CARE VERY EXOTHERMIC). The coolant was removed and the suspension was stirred at ambient temperature for 30 minutes and then heated at reflux for 18 hours. The suspension was allowed to cool and carefully quenched with water (750 mL). The mixture was washed with diethyl ether (2×500 mL) and the combined organic phases were discarded. The pH of the aqueous phase was adjusted to 1 with concentrated HCl. The resultant suspension was filtered and the filter-cake washed with water (500 mL). The solid residue was dissolved in chloroform (750 mL) and then washed with saturated brine (750 mL). The organic phase was then dried over magnesium sulfate and the filtrate was evaporated at reduced pressure to give the title compound as a white solid (57.25 g, 83%). $^1$H NMR (CDCl$_3$) 10.0–9.00 (1H, br s), 4.09 (2H, br s), 2.20 (3H, br s), 1.78–1.77 (6H, m), 1.70–1.58 (6H, m).

Step b. 5-[2-(Adamantan-1-yloxy)-1-hydroxy-ethylidene]-2,2-dimethyl-[1,3]dioxane4,6-dione A solution of (adamantan-1-yloxy)-acetic acid (32.3 g, 153 mmol) and 1,1'-carbonyl-diimidazole (27.6 g, 170 mmol) in DCM (600 mL) was stirred at 0° C. for 15 minutes, then at room temperature for 75 minutes. The mixture was concentrated in vacuo (~300 mL) and the solution was then added dropwise, over 20 minutes, to a solution of 2,2-dimethyl-1,3-dioxan-4,6-dione (22.1 g, 153 mmol) and pyridine (30 mL, 371 mmol) in DCM (450 mL) at 0° C. under argon. The mixture was allowed to warm to room temperature and stirred for 16 hours. The organic solution was washed with 2N HCl (2×500 mL), brine (500 mL) and dried (MgSO$_4$). The filtrate was evaporated and the residue triturated with hexane to give the title compound as a white solid (50.1 g, 97%). $^1$H NMR (CDCl$_3$) 4.91 (2H, s), 2.18 (3H, br s), 1.81–1.81 (6H, m), 1.73 (6H, s), 1.68–1.58 (6H, m).

Step c. 5-[4-(Adamantan-1-yloxy)-3-oxo-butyrylamino]-benzoic acid methyl ester.

A mixture of 5-[2-(adamantan-1-yloxy)-1-hydroxy-ethylidene]-2,2-dimethyl-[1,3]dioxane-4,6-dione (27.27 g, 81.1 mmol), 3-amino-benzoic acid methyl ester (11.68 g, 77.2 mmol) and DMAP (cat.) in benzene (550 mL) was heated at reflux for 2 hours. The mixture was allowed to cool to room temperature. The solvent was removed by evaporation at reduced to give the crude product as a red oil. Purification by flash column chromatography (DCM:ethyl acetate 6:1) yielded the title compound as a yellow foam (20.34 g, 68%). $^1$H NMR (CDCl$_3$) 9.22 (1H, br s), 8.08–8.07 (1H, t), 7.91–7.88 (1H, m), 7.81–7.77 (1H, m), 7.43–7.38 (1H, m), 4.14 (2H, s), 3.91 (3H, s), 3.74 (2H, s), 2.19 (3H, br s), 1.83–1.58 (12H, m).

Step d. 3-[4-(Adamantan-1-yloxy)-2-hydroxyimino-3-oxo-butyrylamino]-benzoic acid methyl ester To a solution of 3-[4-(adamantan-1-yloxy)-3-oxo-butyrylamino]-benzoic acid methyl ester (9.95 g, 25.8 mmol) in acetic acid (100 mL) and THF (90 mL) was added water (12 mL). The mixture was cooled to 5° C. and an aqueous solution (16 mL) of sodium nitrite (2.31 g, 35.0 mmol) was added dropwise while maintaining the temperature below 10° C. Upon completion of the addition, the reaction mixture was allowed to warm to room temperature and stirred for 1 h. The solvent was removed under reduced pressure and the residue was partitioned between saturated aqueous NaHCO$_3$ and ethyl acetate. The aqueous phase was discarded and the organic phase was washed with further saturated aqueous NaHCO$_3$ and brine. The organic phase was dried (MgSO$_4$) and the solvent was evaporated at reduced pressure to afford the title product as a yellow foam (10.15 g, 95%). $^1$H NMR (CDCl$_3$) 11.06 (1H, br s), 8.25 (1H, s), 7.93–7.90 (1H, m), 7.84–7.81 (1H, m), 7.51–7.41 (1H, m), 4.83 (2H, s), 3.95 (3H, s), 2.20 (3H, s), 1.82–1.57 (12H, m).

General Synthesis of the 2-Substituted 3-{[5-(adamantan-1-yloxymethyl)-2H-[1,2,3]triazole-4-carbonyl]-amino}-benzoic acids and the Corresponding 1-Substituted 3-{[5-(adamantan-1-yloxymethyl)-1H-[1,2,3]triazole-4-carbonyl]-amino}-benzoic acids.

Triethylamine (1.5 eq) was added to a stirred suspension of 3-[4-(adamantan-1-yloxy)-2-hydroxyimino-3-oxo-butyrylamino]-benzoic acid methyl ester (1.0 eq) and the appropriate hydrazine-hydrochloride (1.5 eq) in ethanol (4 mL per mmol). The resultant solution was stirred at room temperature for 18 hours. The reaction mixture was diluted with ethyl acetate and was washed sequentially with 2M HCl and brine. The organic phase was dried (MgSO$_4$) and the filtrate was evaporated at reduced pressure. The residue was dissolved in DCM (10 mL per mmol) and the solution was cooled in ice/water. 1,8-Diazabicyclo[5.4.0]undec-7-ene (1.2 eq) and p-toluenesulfonyl chloride (1.1 eq) were added sequentially, the coolant removed and the reaction mixture was stirred at room temperature for 40 minutes. The reaction mixture was re-cooled in ice/water and further 1,8-diazabicyclo[5.4.0]undec-7-ene (1.2 eq) was added. The coolant was removed and the reaction mixture was stirred at room temperature for 18 h. The reaction mixture was washed sequentially with 2M HCl, saturated aqueous sodium hydrogen carbonate and brine. The organic phase was dried (MgSO$_4$) and the filtrate evaporated at reduced pressure. The residue was purified by flash column chromatography (DCM:EtOAc 20:1) to recover the methyl esters of the 2-substituted 3-{[5-(adamantan-1-yloxymethyl)-2H-[1,2,3]triazole-4-carbonyl]-amino}-benzoic acids as the higher $R_f$ material. Further elution, where applicable, gave rise to the isomeric methyl esters of the 1-substituted 3-{[5-(adamantan-1-yloxymethyl)-1H-[1,2,3]triazole-4-carbonyl]-amino}-benzoic acids. The methyl ester was taken-up in THF/water (10 mL per mmol of each) and treated with lithium hydroxide-monohydrate (5 eq). The reaction mixture was stirred at room temperature for 18 h. The reaction mixture was diluted with equal parts of ethyl acetate and 2M HCl. The aqueous phase was discarded and the organic phase was washed with brine and then dried (MgSO$_4$). The filtrate was evaporated at reduced pressure to afford the title compounds. The title compounds were converted to their N-methyl D-glucamine salts for microanalysis and biological evaluation.

EXAMPLE 1

3-[[5-(Adamantan-1-yloxymethyl)-2-(2-methyl-phenyl)-2H-[1,2,3]triazole-4-carbonyl]-amino]-benzoic acid $^1$H NMR (DMSO-d$_6$) 13.00 (1H, br s), 10.60 (1H, s), 8.40 (1H, s), 8.00 (1H, d), 7.70 (2H, m), 7.50 (4H, m), 4.90 (2H, s), 2.30 (3H, s), 2.10 (3H, s), 1.8 (6H, s), 1.60 (6H, s).

Microanalysis; found: C, 60.12; H, 6.94; H, 10.01%; C$_{28}$H$_{30}$N$_4$O$_4$—C$_7$H$_{17}$NO$_5$—H$_2$O requires: C, 60.07; H, 7.06; N, 10.01%.

EXAMPLE 2

3-[[5-(Adamantan-1-yloxymethyl)-2-cyclohexyl-2H-[1,2,3]triazole-4-carbonyl]-amino]-benzoic acid $^1$H NMR (DMSO-d$_6$) 8.40 (1H, s), 8.00 (1H, d), 7.70 (1H, d), 7.50 (1H, t), 4.70 (2H, s), 4.50 (1H, m), 2.00–1.20 (25H, m). Microanalysis; found: C, 57.59; H, 7.87; N, 9.83%; C$_{27}$H$_{34}$N$_4$O$_4$—C$_7$H$_{17}$NO$_5$-2H$_2$O requires: C, 57.53; H, 7.81; N, 9.87%.

EXAMPLE 3

3-[[5-(Adamantan-1-yloxymethyl)-2-(2,6-dichlorophenyl)-2H-[1,2,3]triazole-4-carbonyl]-amino]-benzoic acid $^1$H NMR (DMSO-d$_6$) 10.75 (1H, br s), 8.47 (1H, br s), 7.99 (1H, d), 7.84–7.68 (4H, m), 7.50–7.45 (1H, m), 4.92 (2H, s), 2.10 (3H, s) 1.77–1.76 (6H, m), 1.63–1.53 (6H, m).

Microanalysis; found: C, 52.88; H 5.99; N 9.04%; C$_{27}$H$_{26}$Cl$_2$N$_4$O$_4$—C$_7$H$_{17}$NO$_5$-2H$_2$O requires: C, 52.85; H, 6.13; N, 9.06%.

EXAMPLE 4

3-[[5-(Adamantan-1-yloxymethyl)-2-(2,4,6-trichlorophenyl)-2H-[1,2,3]triazole-4-carbonyl]-amino]-benzoic acid $^1$H NMR (CDCl$_3$) 9.72 (1H br s), 8.34–8.21 (2H, m), 7.92–7.89 (1H, m), 7.54–7.49 (3H, m), 5.07 (2H, s), 2.20 (3H, s), 1.92–1.91 (6H, m), 1.70–1.65 (6H, m). Microanalysis; found: C, 51.59; H, 5.90; N, 8.66%; C$_{27}$H$_{25}$Cl$_3$N$_4$O$_4$—C$_7$H$_{17}$NO$_5$—H$_2$O requires: C, 51.75; H, 5.62; N, 8.88%.

EXAMPLE 5

3-[[5-(Adamantan-1-yloxymethyl)-2-(2-chloro-phenyl)-2H-[1,2,3]triazole-4-carbonyl]-amino]-benzoic acid $^1$H NMR (DMSO-d$_6$) 13.00 (1H, br s), 10.70 (1H, s), 8.45 (1H,s), 7.96–7.47 (6H, m), 4.88 (2H, s) 2.10 (3H,s), 1.77 (6H, s), 1.58 (6H, s). Microanalysis; found: C, 56.79; H, 6.38; 9.66%; C$_{27}$H$_{27}$ClN$_4$O$_4$—C$_7$H$_{17}$NO$_5$—H$_2$O requires: C, 56.86; H, 6.18; N, 9.75%.

EXAMPLE 6

3-[[5-(Adamantan-1-yloxymethyl)-1-(2-chloro-phenyl)-1H-[1,2,3]triazole-4-carbonyl]-amino]-benzoic acid $^1$H NMR (DMSO-d$_6$) 13.00 (1H, br s), 11.20 (1H, br s), 8.45 (1H, br s), 7.89–7.43 (7H, m), 4.60 (2H, s), 2.13 (3H, br s), 1.78 (6H, s), 1.60 (6H, s). Microanalysis; found C, 56.22; H, 6.49; N, 9.33; C$_{27}$H$_{27}$ClN$_4$O$_4$—C$_7$H$_{17}$NO$_5$-1.5H$_2$O requires: C, 56.16; H, 6.24; N, 9.63.

EXAMPLE 7

3-[[5-(Adamantan-1-yloxymethyl)-2-(2-trifluoromethyl-phenyl)-2H-[1,2,3]triazole-4-carbonyl]-amino]-benzoic acid $^1$H NMR (DMSO-d$_6$) 10.70 (1H, br s), 8.44 (1H, s), 8.06–7.85 (5H, m) 7.71 (1H, d), 7.48 (1H, t), 4.87 (2H, s), 2.10 (3H, s), 1.76–1.75 (6H, m), 1.57 (6H, s). Microanalysis; found: C, 55.01; H, 6.33; N, 9.24%; C$_{28}$H$_{27}$F$_3$N$_4$O$_4$—C$_7$H$_{17}$NO$_5$-1.5 H$_2$O requires: C, 55.11; H, 6.21; N, 9.18%.

EXAMPLE 8

3-[[5-(Adamantan-1-yloxymethyl)-2-(2-ethyl-phenyl)-2H-[1,2,3]triazole-4-carbonyl]-amino]-benzoic acid $^1$H NMR (DMSO-b$_6$) 13.00 (1H, br s), 10.60 (1H, br s), 10.60 (1H,s), 8.00–7.97 (1H, d), 7.70–7.41 (6H, m), 4.88 (2H, s), 2.63 (2H, q), 2.10 (3H, s), 1.77–1.76 (6H, m), 1.62–1.53 (6H, m), 1.06 (3H, t). Microanaylsis; found: C, 60.60; H 7.24; N, 9.92%; C$_{29}$H$_{32}$N$_4$O$_4$—C$_7$H$_{17}$NO$_5$—H$_2$O requires: C, 60.57; H, 7.20; N, 9.81%.

EXAMPLE 9

3-[[5-(Adamantan-1-yloxymethyl)-2-tert-butyl-2H-[1,2,3]triazole-4-carbonyl]-amino]-benzoic acid $^1$H NMR (DMSO-d$_6$) 13.00 (1H, br s), 10.30 (1H, br s), 8.36 (1H, m), 8.02–7.99 (1H, m), 7.69–7.67 (1H, m), 7.50–7.45 (1H, m) 4.73 (2H, s), 2.09 (3H, s), 1.77–1.52 (21H, m).

Microanalysis; found: C, 57.77; H, 7.89; N, 10.44%; C$_{25}$H$_{32}$N$_4$O$_4$—C$_7$H$_{17}$NO$_5$—H$_2$O requires: C, 57.73; H, 7.72; N, 10.52%.

EXAMPLE 10

3-[[5-(Adamantan-1-yloxymethyl)-2-(2-methoxyphenyl)-2H-[1,2,3]triazole-4-carbonyl]amino]-benzoic acid $^1$H NMR (DMSO-$_6$) 13.00 (1H, br s), 10.60 (1H, br s), 8.45 (1H, s), 7.98 (1H, d) 7.69–7.67 (1H, m), 7.62–7.56 (2H, m) 7.49–7.44 (1H, m), 7.33 (1H, d), 7.14 (1H, t), 4.84 (2H, s), 3.81 (3H, s), 2.11 (3H, s), 1.77 (6H, s), 1.58 (6H, s). Microanalysis; found: C, 56.67; H, 7.32; N, 9.31%; $C_{28}H_{30}N_4O_4$—$C_7H_{17}NO_5$-2.5 $H_2O$ requires: C, 56.59; H, 7.06; N, 9.43%.

EXAMPLE 11

Endo-3-[[5-(Adamantan-1-yloxymethyl)-2-bicyclo[2.2.1]hept-2-yl-2H-[1,2,3]triazole-4-carbonyl]-amino]-benzoic acid $^1$H NMR (DMSO-d$_6$) 12.89 (1H, br s), 10.35 (1H, s), 8.38 (1H, s), 8.00 (1H, d), 7.69 (1H, d), 7.50–7.44 (1H, t), 5.00–4.97 (1H, m), 4.75 (2H, s), 2.73 (1H, m), 2.36 (1H, s) 2.25–2.09 (5H, m), 1.65–1.29 (11H, m), 0.95–0.92 (1H, m). Microanalysis; found: C, 58.33; H, 7.88; N, 9.89%; $C_{28}H_{34}N_4O_4$—$C_7H_{17}NO_5$-2$H_2O$ requires: C, 58.24; H, 7.68; N, 9.70%.

EXAMPLE 12

3-[[5-(Adamantan-1-yloxymethyl)-2-(2-fluorophenyl)-2H-[1,2,3]triazole-4-carbonyl]-amino]-benzoic acid $^1$H NMR (DMSO-d$_6$) 13.00 (1H, br s), 10.70 (1H, br s), 8.44 (1H, s), 8.00–7.91 (2H, m), 7.71–7.46 (5H, m), 4.86 (2H, s), 2.10 (3H, s), 1.77–1.76 (6H, m), 1.62–1.53 (6H, m). Microanalysis; found: C, 58.76; H, 6.74; N, 9.87%; $C_{27}H_{27}FN_4O_4$—$C_7H_{17}NO_5$-0.5 $H_2O$ requires: C, 58.78; H, 6.53; N, 10.08%.

EXAMPLE 13

3-[[5-(Adamantan-1-yloxymethyl)-2-(2-bromophenyl)-2H-[1,2,3]triazole-4-carbonyl]-amino]-benzoic acid $^1$H NMR (DMSO-d$_6$) 13.00 (1H, br s), 10.70 (1H, s), 8.46 (1H, s), 7.97–7.47 (7H, m) 4.88 (2H, s), 2.11 (1H, s), 1.78–1.77 (6H, m), 1.58 (6H, s). Microanalysis; found: C, 53.38; H, 6.08; N, 8.84%; $C_{27}H_{27}BrN_4O_4$—$C_7H_{17}NO_5$—$H_2O$ requires: C, 53.40; H, 6.06; N, 9.16%.

EXAMPLE 14

3-[[5-(Adamantan-1-yloxymethyl)-1-(2-bromophenyl)-1H-[1,2,3]triazole-4-carbonyl]-amino]-benzoic acid $^1$H NMR (DMSO-d$_6$) 12.8 (1H, br s), 11.1 (1H, br s), 8.41–8.40 (1H, m), 7.83–7.43 (7H, m), 4.60 (2H, s), 2.13 (3H, br s), 1.79 (6H, s), 1.60 (6H, s). Microanalysis; found: C, 54.41; H, 6.04; N, 9.18%; $C_{27}H_{27}BrN_4O_4$—$C_7H_{17}NO_5$ requires: C, 54.69; H, 5.94; N, 9.38%.

EXAMPLE 15

3-[[5-(Adamantan-1-yloxymethyl)-2-cycloheptyl-2H-[1,2,3]triazole-4-carbonyl]-amino]-benzoic acid $^1$H NMR (DMSO-d$_6$) 12.90 (1H, br s), 10.40 (1H br s), 8.40 (1H, s), 7.99–7.96 (1H, m), 7.69 (1H, d), 7.49–7.44 (1H, m), 4.80–4.71 (3H, m), 2.12–2.06 (7H, m), 1.77–1.52 (20H, m).

Microanalysis; found: C, 59.64; H, 7.99; N, 9.87%; $C_{28}H_{36}N_4O_4$—$C_7H_{17}NO_5$—$H_2O$ requires: C, 59.56; H, 7.85; N, 9.92%.

EXAMPLE 16

3-[[2-Adamantan-2-yl-5-(Adamantan-1-yloxymethyl)-2H-[1,2,3]triazole-4-carbonyl]-amino]-benzoic acid.

$^1$H NMR (DMSO-d$_6$) 12.80 (1H, br s),10.37–10.32 (1H, br s), 8.41–8.38 (1H, m), 0.05–7.98 (1H, m), 7.71–7.67 (1H, m), 7.53–7.44 (1H, m), 4.77 (2H, s), 4.62 (1H, s), 3.86 (2H, s), 2.79 (2H, s), 2.09–1.56 (25H, m). Microanalysis; found: C, 61.22; H, 7.90; N, 9.31%; $C_{31}H_{38}N_4O_4$—$C_7H_{17}NO_5$—$H_2O$ requires: C, 61.35; H, 7.72; N, 9.41%.

EXAMPLE 17

3-[[5-(Adamantan-1-yloxymethyl)-2-(2-isopropylphenyl)-2H-[1,2,3]triazole-4-carbonyl]-amino]-benzoic acid $^1$H NMR (DMSO-d$_6$) 13.00 (1H, br s), 10.60 (1H, br s), 8.44 (1H, s), 7.97–7.96 (1H, m), 7.70–7.35 (6H, m), 4.88 (2H, s), 2.90–2.87 (1H, m), 2.10 (3H, s), 1.77–1.76 (6H, m), 1.58 (6H, s), 1.17 (6H, d). Microanalysis; found: C, 60.49; H, 7.49; N, 9.38%; $C_{30}H_{34}N_4O_4$—$C_7H_{17}NO_5$-1.5 $H_2O$ requires: C, 60.31; H, 7.39; N, 9.50%.

EXAMPLE 18

3-[[5-(Adamantan-1-yloxymethyl)-2-naphthalen-1-yl-2H-[1,2,3]triazole-4-carbonyl]-amino]-benzoic acid $^1$H NMR (DMSO-d$_6$) 9.56 (1H, br s), 8.26–8.22 (2H, m), 8.20–8.10 (1H, m), 8.00–7.85 (4H, m), 7.63–7.25 (4H, m), 5.11 (2H, s), 2.23 (3H, s), 1.98–1.97 (6H, m), 1.68 (6H, s). Microanalysis; found: C, 62.04; H, 6.80; N, 9.33%; $C_{31}H_{30}N_4O_4$—$C_7H_{17}NO_5$-1 $H_2O$ requires: C, 62.03; H, 6.79; N, 9.52%.

EXAMPLE 19

3-[[5-(Adamantan-1-yloxymethyl)-2-(2,3-dimethylphenyl)-2H-[1,2,3]triazole-4-carbonyl]-amino]-benzoic acid $^1$H NMR (DMSO-d$_6$) 13.0 (1H, br s), 10.6 (1H, br s), 8.45–8.44 (1H, m), 8.00–7.96 (1H, m), 7.70–7.67 (1H, m), 7.50–7.31 (4H, m), 4.87 (2H, s), 2.36 (3H, s), 2.10 (3H, br s), 2.08 (3H, s), 1.77–1.75 (6H, m), 1.58 (6H, s). Microanalysis found: C, 59.00; H, 7.48; N, 9.61%; $C_{29}H_{32}N_4O_4$—$C_7H_{17}NO_5$-2 $H_2O$ requires: C, 59.08; H, 7.30; N, 9.57%

EXAMPLE 20

3-[[5-(Adamantan-1-yloxymethyl)-2-phenyl-2H-[1,2,3]triazole-4-carbonyl]-amino]-benzoic acid $^1$H NMR (DMSO-d$_6$) 13.0 (1H, br s), 10.6 (1H, br s), 8.44–8.43 (1H, m), 8.15–8.12 (2H, m), 8.02 (1H, m), 7.72–7.69 (1H, m), 7.65–7.60 (2H, m), 7.53–7.48 (2H, m), 4.86 (2H, s), 2.11 (3H, br s), 1.78–1.77 (6H, m), 1.58 (6H, s). Microanalysis found: C, 57.91; H, 7.25; N, 9.88%; $C_{27}H_{28}N_4O_4$—$C_7H_{17}NO_5$-2 $H_2O$ requires: C, 58.02; H, 7.02; N, 9.95%.

EXAMPLE 21

3-[[5-(Adamantan-1-yloxymethyl)-2-(biphenyl-2-yl)-2H-[1,2,3]triazole-4-carbonyl]-amino]-benzoic acid $^1$H NMR (DMSO-$_6$) 13.0 (1H, br s), 10.5 (1H, br s), 8.41 (1H, m), 7.93 (1H, m), 7.73–7.61 (5H, m), 7.46 (1H, m), 7.30–7.28 (3H, m), 7.11–7.08 (2H, m), 4.71 (2H, s), 2.05 (3H, br s), 1.62–1.49 (12, m). Microanalysis found: C, 63.01; H, 6.85; N, 9.07%; $C_{33}H_{32}N_4O_4$—$C_7H_{17}NO_5$—$H_2O$ requires: C, 63.06; H, 6.75; N, 9.19%.

EXAMPLE 22

3-[[5-(Adamantan-1-yloxymethyl)-2-(2,5-dimethyl-phenyl)-2H-[1,2,3]triazole-4-carbonyl]-amino]-benzoic acid $^1$H NMR (DMSO-$d_6$) 12.9 (1H, br s), 10.6 (1H, br s), 8.44 (1H, s), 8.01–7.98 (1H, m), 7.71–7.68 (1H, d, J=9 Hz), 7.50–7.45 (2H, m), 7.36–7.28 (2H, m), 4.86 (2H, s), 2.36 (3H, s), 2.29 (3H, s), 2.10 (3H, br s), 1.77–1.76 (6H, m), 1.56 (6H, s). Microanalysis found: C, 60.33; H, 7.39; N, 9.76%; $C_{29}H_{32}N_4O_4$—$C_7H_{17}NO_5$—$H_2O$ requires: C, 60.57; H, 7.20; N, 9.81%.

EXAMPLE 23

3-[[5-(Adamantan-1-yloxymethyl)-2-(2,5-dichloro-phenyl)-2H-[1,2,3]triazole-4-carbonyl]-amino]-benzoic acid $^1$H NMR (DMSO-$d_6$) 13.0 (1H, br s), 10.7 (1H, br s), 8.45 (1H, s), 7.98–7.94 (2H, m), 7.85–7.82 (1H, m), 7.71–7.61 (2H, m), 7.50–7.45 (1H, m), 4.88 (2H, s), 2.10 (3H, br s), 1.77–1.76 (6H, m), 1.58 (6H, s). Microanalysis found: C, 52.66; H, 6.18; N, 9.11%; $C_{27}H_{26}Cl_2N_4O_4$—$C_7H_{17}NO_5$-2 $H_2O$ requires: C, 52.85; H, 6.13; N, 9.06%.

EXAMPLE 24

3-[[5-(Adamantan-1-yloxymethyl)-1/2/3H-[1,2,3]triazole-4-carbonyl]-amino]-benzoic acid $^1$H NMR (DMSO-$d_6$) 12.8 (1H, br s), 10.59+10.49 (1H, br s), 8.55–8.44 (1H, m), 7.85+7.95 (1H, m), 7.67–7.65 (1H, m), 7.47–7.41 (1H, m), 4.91+4.77 (2H, s), 2.11 (3H, br s), 1.76 (6H, s), 1.58 (6H, s). Microanalysis found: C, 52.09; H, 7.31; N, 10.98%; $C_{21}H_{24}N_4O_4C_7H_{17}NO_5$-3 $H_2O$ requires: C, 52.08; H, 7.34; N, 10.85%.

EXAMPLE 25

3-[[5-(Adamantan-1-yloxymethyl)-2-(2,4-dimethyl-phenyl)-2H-[1,2,3]triazole-4-carbonyl]-amino]-benzoic acid $^1$H NMR (DMSO-$d_6$) 13.0 (1H, br s), 10.6 (1H, br s), 8.43 (1H, s), 8.00 (1H, d, J=9 Hz), 7.70 (1H, d, J=6 Hz), 7.53–7.45 (2H, m), 7.28–7.21 (2H, m), 4.86 (2H, s), 2.37 (3H, s), 2.29 (3H, s), 2.10 (3H, br s), 1.77–1.76 (6H, m), 1.58 (6H, s). Microanalysis found: C, 59.79; H, 7.46; N, 9.48%; $C_{29}H_{32}N_4O_4$—$C_7H_{17}NO_5$-1.5 $H_2O$ requires: C, 59.82; H, 7.25; N, 9.69%.

EXAMPLE 26

3-[[5-(Adamantan-1-yloxymethyl)-2-(2-nitro-phenyl)-2H-[1,2,3]triazole-4-carbonyl]-amino]-benzoic acid $^1$H NMR (DMSO-$d_6$) 12.9 (1H, br s), 10.7 (1H, br s), 8.42 (1H, s), 8.20–8.17 (1H, m), 8.11–8.07 (1H, m), 7.98–7.95 (2H, m), 7.86–7.83 (1H, m), 7.72–7.69 (1H, m), 7.52–7.49 (1H, m), 4.84 (2H, s), 2.10 (3H, br s), 1.75–1.74 (6H, m), 1.61–1.53 (6H, m).

Microanalysis found: C, 55.88; H, 6.74; N, 11.35%; $C_{27}H_{27}N_5O_6$—$C_7H_{17}NO_5$—$H_2O$ requires: C, 55.88; H, 6.35; N, 11.50%.

EXAMPLE 27

3-[[5-(Adamantan-1-yloxymethyl)-2-(2-nitro-phenyl)-2H-[1,2,3]triazole-4-carbonyl]-amino]-benzoic acid.

To a degassed solution of 3-[[5-(adamantan-1-yloxymethyl)-2-(2-nitro-phenyl)-2H-[1,2,3]triazole-4-carbonyl]-amino}-benzoic acid (132 mg, 0.26 mmol) in dioxan/ethyl acetae/methanol (5 mL each) was added palladium on charcoal (10%, 27 mg). The resultant suspension was stirred under a hydrogen atmosphere (via balloon) for 24 h. The suspension was filtered and the filter-cake washed with further ethyl acetate (15 mL). The filtrate was evaporated to yield the title compound (101 mg, 100%). $^1$H NMR (DMSO-$d_6$) 12.9 (1H, br s), 10.6 (1H, br s), 8.40 (1H, m), 8.00 (1H, m), 7.73–7.69 (2H, m) 7.50 (1H, t J=9 Hz), 7.19–7.17 (1H, m), 6.99–6.96 (1H, m), 6.71–6.68 (1H, m), 6.14 (2H, br s), 4.87 (2H, s), 2.11 (3H, br s), 1.78–1.77 (6H, m), 1.59 (6H, s). The material was further analysed as its N-methyl D-glucamine salt. Microanalysis found: C, 58.07; H, 7.08; N, 11.74%; $C_{27}H_{29}N_5O_4$—$C_7H_{17}NO_5$—$H_2O$ requires: C, 58.27; H, 6.90; N, 11.99%.

EXAMPLE 28

3-{[2-(2,6-Dichloro-phenyl)-5-phenoxymethyl-2H-[1,2,3]triazole-4-carbonyl]-amino}-benzoic acid Step a. 2-Hydroxyimino-3-oxo-4-phenoxy-butyric acid ethyl ester.

To an ice-cooled solution of 3-oxo-4-phenoxy-butyric acid ethyl ester[1] (2.22 g, 10.0 mmol) in acetic acid (40 mL), THF (35 mL) and water (4 mL) was added dropwise a solution of sodium nitrite (896 mg, 13.0 mmol) in water (6 mL). The coolant was removed and the reaction mixture was stirred at ambient temperature for 75 minutes. The solvent was removed in vacuo and the residue partitioned between ethyl acetate (100 mL) and saturated aqueous sodium hydrogen carbonate (100 mL). The aqueous phase was discarded and the organic phase was washed with brine (100 mL). The organic phase was dried over magnesium sulfate and the filtrate evaporated at reduced pressure to yield the title compound. The crude material was used without any further purification.

Step b. 2-(2,6-Dichloro-phenyl)-5-phenoxymethyl-2H-[1,2,3]triazole-4-carboxylic acid ethyl ester Triethylamine (2.09 mL, 15.0 mmol) was added to a stirred suspension of the product from step a (10.0 mmol) and 2,6-dichlorophenylhydrazine-hydrochloride (3.20 g, 10.0 mmol) in ethanol (30 mL). The resultant solution was stirred at room temperature for 18 hours. The reaction mixture was diluted with ethyl acetate and was washed sequentially with 2M HCl and brine. The organic phase was dried (MgSO$_4$) and the filtrate was evaporated at reduced pressure. The residue was dissolved in DCM (100 mL) and the solution was cooled in ice/water. 1,8-Diazabicyclo [5.4.0]undec-7-ene (1.84 mL, 12.3 mmol) and p-toluenesulfonyl chloride (2.14 g, 11.2 mmol) were added sequentially, the coolant removed and the reaction mixture was stirred at room temperature for 40 minutes. The reaction mixture was re-cooled in ice/water and further 1,8-diazabicyclo[5.4.0]undec-7-ene (1.84 mL, 12.3 mmol) was added. The coolant was removed and the reaction mixture was stirred at room temperature for 18 h. The reaction mixture was washed sequentially with 2M HCl, saturated aqueous sodium hydrogen carbonate and brine. The organic phase was dried (MgSO$_4$) and the filtrate evaporated at reduced pressure. The residue was purified by flash column chromatography (2:1 hexane:ethyl acetate) to recover the title compound (1.44 g, 37%). $^1$H NMR (CDCl$_3$) 7.48–7.44 (3H, m), 7.32–7.27 (2H, m), 7.08–6.98 (3H, m), 5.52 (2H, s), 4.49 (2H, q, J=7.2 Hz), 1.41 (3H, t, J=7.2 Hz).

Step c. 2-(2,6-Dichloro-phenyl)-5-phenoxymethyl-2H-[1,2,3]triazole-4-carboxylic acid A solution of the product from step b (1.43 g, 3.65 mmol) and potassium hydroxide (632 mg, 11.3 mmol) in ethanol/water (14 mL/2 mL) was heated at reflux for 2 h. The reaction mixture was allowed to cool and diluted with water (30 mL). The reaction mixture was washed with ether (30 mL) and the organic phase was discarded. The pH of the aqueous phase was adjusted to 1 with aqueous 2M hydrochloric acid and extracted twice with chloroform (40 mL). The combined chloroform extracts were dried (MgSO$_4$) and the filtrate evaporated at reduced pressure to afford the title compound (1.16 g, 87%). $^1$H NMR (CDCl$_3$) 7.52 (3H, m), 7.33–7.27 (2H, m), 7.08–6.99 (3H, m), 5.54 (2H, s).

Step d. 3-{[2-(2,6-Dichloro-phenyl)-5-phenoxymethyl-2H-[1,2,3]triazole-4-carbonyl]-amino}-benzoic acid methyl ester.

EDC (869 mg, 4.53 mmol) was added to a stirred solution of the product from step c (1.10 g, 3.02 mmol), methyl 3-aminobenzoate (685 mg, 4.53 mmol), N-hydoxybenzotriazole (612 mg, 4.53 mmol) and 4-DMAP (cat) in DMF (10 ml). The solution was stirred for 72 h and then diluted with ethyl acetate (40 mL). The solution was washed sequentially with water (40 mL) and twice with brine (40 mL). The organic phase was dried (MgSO$_4$) and the filtrate was evaporated at reduced pressure. The residue was purified by flash column chromatography (100% DCM) to yield the title compound (935 mg, 62%). $^1$H NMR (CDCl$_3$) 8.71 (1H, br s), 8.21–8.20 (1H, t, J=1.8 Hz), 8.05–8.02 (1H, m), 7.86–7.83 (1H, m), 7.54–7.43 (4H, m), 7.31–7.26 (2H, m), 7.11–7.07 (2H, m), 7.00–6.97 (1H, m), 5.65 (2H, s), 3.92 (3H, s).

Step e. 3-{[2-(2,6-Dichloro-phenyl)-5-phenoxymethyl-2H-1,2,3]triazole-4-carbonyl]-amino}-benzoic acid Lithium hydroxide monohydrate (386 mg, 9.20 mmol) was added to a solution of the product from step d (915 mg, 1.84 mmol) in THF/water (18 mL each). The reaction mixture was stirred at ambient temperature for 18 h. The reaction mixture was partitioned between ethyl acetate (40 mL) and 2M aqueous hydrochloric acid (40 mL). The aqueous phase was discarded and the organic phase was washed with brine (40 mL) and dried (MgSO$_4$). The filtrate was evaporated to yield the title compound (841 mg, 95%). $^1$H NMR (DMSO-d$_6$) 12.9 (1H, br s), 10.9 (1H, br s), 8.51 (1H, m), 7.97 (1H, m), 7.84–7.68 (4H, m), 7.49–7.46 (1H, m), 7.32–7.26 (2H, m), 7.05–6.95 (3H, m), 5.56 (2H, s). The material was further analysed as its N-methyl D-glucamine salt. Microanalysis found: C, 52.76; H, 4.98; N, 9.99%; C$_{23}$H$_{16}$Cl$_2$N$_4$O$_4$—C$_7$H$_{17}$NO$_5$-0.5H$_2$O requires: C, 52.41; H, 4.98; N, 10.17%.

EXAMPLE 29

3-{[5-Cycloheptyloxymethyl-2-(2,6-dichloro-phenyl)-2H-[1,2,3]triazole-4-carbonyl]-amino}-benzoic acid Step a. 4-Cycloheptyloxy-3-oxo-butyric acid ethyl ester Ethyl 4-chloroacetoacetate (3.00 mL, 22.1 mmol) was added dropwise to an ice-cooled suspension of sodium hydride (60% dispersion in oil, 2.04 g, 51.0 mmol) in DME (20 mL). Immediately cycloheptanol (3.00 mL, 24.9 mmol) was added dropwise and the resultant reaction mixture was allowed to warm slowly to ambient temperature and then stirred at this temperature for 18 h. The reaction mixture was quenched with aqueous 2M hydrochloric acid (100 mL) and extracted with ethyl acetate (100 mL). The aqueous phase was discarded and the organic phase washed with brine (100 mL) and dried (MgSO$_4$). The residue was purified by flash column chromatography (4:1 hexane:ethyl acetate) to afford the tide compound (4.51 g, 84%). $^1$H NMR (CDCl$_3$) 4.23–4.16 (2H, m), 4.07 (2H, s), 3.55 (2H, s), 3.50–3.47 (1H, m), 1.88–1.87 (2H, m), 1.67–1.53 (8H, m), 1.31–1.26 (5H, m).

Step b. 3-{[5-Cycloheptyloxymethyl-2-(2,6-dichloro-phenyl)-2H-[1,2,3]triazol-e-4-carbonyl]-amino}-benzoic acid The title compound was prepared as in Example 28 with 4-cycloheptyloxy-3-oxo-butyric acid ethyl ester replacing 3-oxo-4-phenoxy-butyric acid ethyl ester in step a.

$^1$H NMR (DMSO-d$_6$) 12.9 (1H, br s), 10.77 (1H, br s), 8.49 (1H, s), 7.97–7.96 (1H, m), 7.84–7.68 (4H, m), 7.49–7.44 (1H, m), 4.90 (2H, s), 3.62–3.60 (1H, m), 2.00–1.80 (2H, m), 1.57–1.40 (10H, m). The material was further analysed as its N-methyl D-glucamine salt.

Microanalysis found: C, 51.79; H, 6.30; N, 9.73%; C$_{24}$H$_{24}$Cl$_2$N$_4$O$_4$—C$_7$H$_{17}$NO$_5$-1 H$_2$O requires: C, 51.96; H, 6.05; N, 9.77%.

EXAMPLE 30

3-{[5-Cyclohexyloxymethyl-2-(2,6-dichloro-phenyl)-2H-[1,2,3]triazole-4-carbonyl]-amino}-benzoic acid The title compound was prepared as in Example 29 with cyclohexanol replacing cycloheptanol in step a.

$^1$H NMR (DMSO-d$_6$) 12.9 (1H, br s), 10.76 (1H, br s), 8.48 (1H, s), 7.96 (1H, m), 7.83–7.67 (4H, m), 7.46 (1H, d, J=9 Hz), 4.93 (2H, s), 3.45–3.43 (1H, m), 1.89–1.83 (2H, m), 1.65–1.63 (2H, m), 1.26–1.14 (5H, m). The material was further analysed as its N-methyl D-glucamine salt. Microanalysis found: C, 51.36; H, 6.04; N, 9.79%; C$_{23}$H$_{22}$Cl$_2$N$_4$O$_4$—C$_7$H$_{17}$NO$_5$-1 H$_2$O requires: C, 51.29; H, 5.88; N, 9.97%.

EXAMPLE 31

(3-{[5-(Adamantan-1-yloxymethyl)-2-(2,6-dichloro-phenyl)-2H-[1,2,3]triazole-4-carbonyl]-amino}-phenyl)acetic acid The title compound was prepared as in Example 28 with 4-adamant-1-yloxy-3-oxo-butyric acid ethyl ester[2] replacing 3-oxo-4-phenoxy-butyric acid ethyl ester in step a, and methyl 3-aminophenylacetic acid replacing methyl 3-aminobenzoic acid in step d.

Prepared as in Example 29 step a with 1-adamantol replacing cyclobentanol.

$^1$H NMR (DMSO-d$_6$) 12.2 (1H, br s), 10.5 (1H, br s), 7.78–7.63 (5H, m), 7.31–7.26 (1H, m), 7.03–7.00 (1H, d, J=9 Hz), 4.91 (2H, s), 3.55 (2H, s), 2.10 (3H, br s), 1.77–1.76 (6H, m), 1.62–1.53 (6H, m). The material was further analysed as its N-methyl D-glucamine salt. Microanalysis found: C, 53.34; H, 6.51; N, 8.75%; C$_{28}$H$_{28}$Cl$_2$N$_4$O$_4$—C$_7$H$_{17}$NO$_5$-2 H$_2$O requires: C, 53.44; H, 6.28; N, 8.90%.

General Synthesis of the Remaining Two Isomeric Triazoles of Example 15

Step a. 1-Prop-2-ynyloxy-adamantane.

A mixture of 1-bromoadamantane (10.8 g, 50.2 mmol), propargyl alcohol (30 ml, 515 mmol) and triethylamine (7.0 ml, 50.3 mmol) were heated at reflux for 4 hours. The reaction mixture was diluted with EtOAc (70 ml) and was washed sequentially with water (100 ml) and brine (100 ml).

The organic phase was dried over magnesium sulfate and the filtrate was evaporated to give the title compound (9.64 g, 100%). 1H NMR (CDCl$_3$) 4.14 (2H, d, J=2.4 Hz), 2.36 (1H, t, J=2.4), 2.16 (3H, s), 1.80–1.79 (6H, m), 1.67–1.57 (6H, m).

Step b. 4-(Adamantan-1-yloxy)-but-2-ynoic acid methyl ester.

n-Butyl lithium (1.6 M in hexanes, 14.0 ml, 22.4 mmol) was added to a cooled (−78° C.) solution of the product from step a (3.80 g, 20.0 mmol) in anhydrous THF (14 ml). The cooling bath was removed and was replaced with one containing ice/water and the reaction mixture was stirred at this temperature for 1 hour. The cooling bath was removed and exchanged for a −78° C. cooling bath and methyl chloroformate (1.85 ml, 23.9 mmol) was added dropwise. The reaction mixture was stirred at −78° C. for 25 minutes and then placed in an ice-water cooling bath. The reaction mixture was stirred at this temperature for 3 hours and was then quenched with saturated ammonium chloride (40 ml). The quenched reaction mixture was extracted with EtOAc (30 ml) and the aqueous phase was discarded. The organic phase was washed with brine (40 ml) and then dried over anhydrous magnesium sulfate. The filtrate was evaporated and the residue was purified by flash column chromatography (hexane:EtOAc 4:1) to yield the target compound (1.79 g, 37%).

$^1$H NMR (CDCl$_3$) 4.26 (2H, s), 3.77 (3H, s), 2.17 (3H, s), 1.78–31.77 (6H, m), 1.68–1.57 (6H, m).

Step c. 5-(Adamantan-1-yloxymethyl)-3-cycloheptyl-3H-[1,2,3]triazole-4-carboxylic acid methyl ester and 5-(adamantan-1-yloxymethyl)-1-cycloheptyl-1H-[1,2,3]triazole-4-carboxylic acid methyl ester.

A solution of the product from step b (2.74 g, 11.1 mmol) and cycloheptyl azide (prepared by the reaction of cycloheptyl bromide and sodium azide) (1.54 g, 11.1 mmol) in toluene (14 ml) was heated under reflux for 42 hours. The solvent was removed invacuo and the residue purified by flash column chromatography (hexane:EtOAc 3:1) to yield 5-(adamantan-1-yloxymethyl)-3-cycloheptyl-3H-[1,2,3]triazole-4-carboxylic acid methyl ester (1.53 g, 36%). $^1$H NMR (CDCl$_3$) 5.27–5.21 (1H, m), 4.73 (2H, s), 3.94 (3H, s), 2.20–2.11 (7H, m), 1.86–1.85 (8H, m), 1.69–1.60 (12H, m). Further eluation gave rise to 5-(adamantan-1-yloxymethyl)-1-cycloheptyl-1H-[1,2,3]triazole-4-carboxylic acid methyl ester (2.00 g, 47%). $^1$H NMR (CDCl$_3$) 4.93 (2H, s), 4.74–4.65 (1H, m), 3.94 (3H, s), 2.32–2.04 (8H, m), 2.00–1.54 (19H, m).

EXAMPLE 32

3-{[5-(Adamantan-1-yloxymethyl)-3-cycloheptyl-3H-[1,2,3]triazole-4-carbonyl]-amino}-benzoic acid 5-(Adamantan-1-yloxymethyl)-3-cycloheptyl-3H-[1,2,3]triazole-4-carboxylic acid methyl ester was converted to the corresponding acid (as in Example 28, step c) which was then coupled to methyl 3-aminobenzoate (as in Example 28, step d). Hydrolysis of the methyl ester (as in Example 28, step e) resulted in the preparation of 3-{[5-(adamantan-1-yloxymethyl)-3-cycloheptyl-3H-[1,2,3]triazole-4-carbonyl]-amino}-benzoic acid. $^1$H NMR (d$_6$-DMSO) 13.02 (1H, s), 10.64 (1H, s), 8.29 (1H, s), 7.89 (1H, d, J=9 Hz), 7.73 (1H, d, J=6 Hz), 7.54–7.49 (1H, m), 4.96–4.92 (1H, m), 4.73 (2H, s), 2.10–2.02 (7H, m), 1.78–1.45 (20H, m). The material was further analysed as its N-methyl D-glucamine salt.

Microanalysis found C, 57.97; H, 8.18; N, 9.66; C$_{28}$H$_{36}$N$_4$O$_4$—C$_7$H$_{17}$NO$_5$-2H$_2$O requires: C, 58.06; H, 7.94; N, 9.68.

EXAMPLE 33

3-{[5-(Adamantan-1-yloxymethyl)-1-cycloheptyl-1H-[1,2,3]triazole-4-carbonyl]-amino}-benzoic acid 5-(Adamantan-1-yloxymethyl)-1-cycloheptyl-3H-[1,2,3]triazole-4-carboxylic acid methyl ester was converted to the corresponding acid (as in Example 28, step c) which was then coupled to methyl 3-aminobenzoate (as in Example 28, step d). Hydrolysis of the methyl ester (as in Example 28, step e) resulted in the preparation of 3-{[5-(adamantan-1-yloxymethyl)-1-cycloheptyl-3H-[1,2,3]triazole-4-carbonyl]-amino}-benzoic acid. $^1$H NMR (d$_6$-DMSO) 12.91 (1H, s), 10.62 (1H, s), 8.51 (1H, m), 7.98–7.95 (1H, m), 7.68 (1H, d, J=9 Hz), 7.47–7.42 (1H, m), 4.98 (2H, s), 4.71–4.66 (1H, m), 2.48–2.07 (7H, m), 1.80–1.54 (20H, m). The material was further analysed as its N-methyl D-glucamine salt.

Microanalysis found C, 59.38; H, 8.05; N, 9.82; C$_{28}$H$_{36}$N$_4$O$_4$—C$_7$H$_{17}$NO$_5$—H$_2$O requires: C, 59.56; H, 7.85; N, 9.92.

The compounds of the examples were tested for gastrin (CCK$_2$) antagonist activity in an immature rat stomach assay. The procedure was as follows:

The oesophagus of immature rats (33–50 g, ca. 21 days old) was ligated at the level of the cardiac sphincter and the duodenal sphincter was cannulated. The stomach was excised and flushed with ca. 1 ml of unbuffered physiological saline solution. The fundus was punctured and cannulated. A further 4–5 ml of unbuffered solution was flushed through the stomach to ensure the preparation was not leaking. The stomach was lowered into a jacketed organ bath containing 40 ml of buffered solution containing 3×10$^{-8}$ M 5-methylfurmethide, maintained at 37° and gassed vigorously with 95% O$_2$/5% CO$_2$. The stomach was continuously perfused at a rate of 1 ml min$^{-1}$ with unbuffered solution gassed with 100% O$_2$ with the perfusate passing over an internally referenced pH-electrode fixed 12 cm above the stomach.

After 120 min of stabilisation the drugs were added directly to the serosal solution in the organ bath and after a further 60 min cumulative pentagastrin dose-response curves were started. Changes in acid secretion were monitored and the curves analysed according to Black et al, Br. J. Pharmacol., 1985, 86, 581.

The results obtained at gastrin (CCK$_2$) receptors are set out in Table 1.

TABLE 1

| Example No. | Rat stomach pK$_B$ |
| --- | --- |
| 1 | 7.36 ± 0.39 |
| 2 | 7.32 ± 0.26 |
| 3 | 7.88 ± 0.34 |
| 4 | 6.72 ± 0.30 |
| 5 | 7.51 ± 0.28 |
| 6 | 7.03 ± 0.21 |
| 7 | 7.17 ± 0.24 |
| 8 | 7.62 ± 0.28 |
| 9 | 6.20 ± 0.20 |
| 10 | 7.38 ± 0.28 |
| 11 | 8.37 ± 0.22 |
| 12 | 6.76 ± 0.36 |
| 13 | 7.02 ± 0.27 |
| 14 | 6.64 ± 0.27 |
| 15 | 7.87 ± 0.16 |
| 16 | 6.82 ± 0.17 |
| 17 | 6.58 ± 0.28 |

TABLE 1-continued

| Example No. | Rat stomach pK$_B$ |
|---|---|
| 18 | 5.82 ± 0.38 |
| 19 | 7.13 ± 0.25 |
| 20 | 5.68 ± 0.33 |
| 21 | 6.62 ± 0.13 |
| 22 | 6.55 ± 0.32 |
| 23 | 6.82 ± 0.17 |
| 24 | 5.65 ± 0.33 |
| 25 | 6.50 ± 0.30 |
| 26 | 6.42 ± 0.20 |
| 27 | 6.67 ± 0.17 |
| 28 | 5.91 ± 0.17 |
| 29 | 7.01 ± 0.30 |
| 30 | 6.56 ± 0.21 |
| 31 | 5.55 ± 0.21 |
| 32 | 5.43 ± 0.30 |

The compounds of certain examples were also tested in a CCK$_1$ binding assay as follows:

The pancreatata were removed from male guinea-pigs (200–300 g; Dunkin Hartley) and placed in ice-cold HEPES buffer (pH 7.2 @ 21±3° C.). The pancreatata were homogenised in 40 ml ice-cold HEPES buffer using a polytron (Brinkmann, PT10, setting 10) 4×1 second. The homogenate was centrifuged at 39,800 g for 15 min at 4° C. The supernatant was discarded and the pellet re-suspended using a Teflon-in-glass homogeniser in 20 volumes of fresh buffer and re-centrifuged as above. The final pellet was re-suspended using a Teflon-in-glass homogeniser to a tissue concentration of 1 mg.ml$^{-1}$ (original wet weight), and filtered through a 500 μm pore-size Nytex mesh.

The membranes (400 μl; containing 0.375 μM PD134, 308) were incubated for 150 minutes at 21±3° C. in a final volume of 0.5 ml with HEPES buffer containing [$^{125}$I]—CCK$_8$ (S) (50 μl; 200 pM) and competing compound. Total and non-specific binding of [$^{125}$I]—CCK$_8$ (S) were defined using 50 μl of buffer and 50μ of 100 nM L-364,718 respectively. The assay was terminated by rapid filtration through pre-soaked Whatman GF/B filters using a Brandell Cell Harvetser. The filters were washed (3×3 ml) with ice-cold 5 mM Tris HCl (pH 7.4 @ 4° C.) and bound radioactivity was determined by counting (1 min) in a gamma counter.

All of the Examples were found to have a CCK$_1$ pK$_i$ in the range of 5.2 to 6.1.

It is found that the compositions and products of the present invention comprising a compound of formula (I) or (II) and a proton pump inhibitor reduce hyperplasia, associated with administration of proton pump inhibitors. This was measured according to the following experimental protocol.

Animals and Treatment:

40 male SPF Wistar rats (200 g) were divided into 4 treatment groups and 2 strata. The treatment of the 20 rats in the second stratum started 2 weeks after the treatment of the first stratum. The design of the study was completely randomised double blind with individual blinding; all rats were placed in a separate cage. Animals had continuous access to water and food.

Animals were treated once daily during 14 days:

Control group: 1 ml gastrin test drug vehicle+1 ml p.o. (gavage) 0.25% Methocel (Dow Corning)

PPI group: 1 ml gastrin test drug vehicle+1 ml p.o. (gavage) 25 mg/kg Rabeprazole in 0.25% Methocel.

GRA group: 1 ml gastrin test drug+1 ml p.o. (gavage) 0.25% Methocel

GRA-PPI group: 1 ml gastrin test drug +1 ml p.o.(gavage) 25 mg/kg Rabeprazole in 0.25% Methocel.

Gastrin test drug made up to an appropriate dose in physiologically compatible solvent.

Preparation of Tissue:

After removal of the fundus, the stomach were rinsed with phosphate buffered saline prior to fixation with 4% formalin in Millonig buffer. After 4 hours immersion in fixative solutions at room temperature, tissue was rinsed in phosphate buffered saline (PBS), dehydrated and embedded in paraffin using the Leitz paraffin embedding station (Leitz TP 1050; Germany) dehydration module and paraffin embedding module (Leitz EG 1160; Germany).

Cross sections (3 μm thick) of the oxyntic part of the stomach were made at 3 levels, each separated by a distance of 400 μm.

Immunostaining

The following indirect immunofluorescence labeling method was used:

removal of paraffin and rehydratation of the sections followed by a blocking step primary antibodies: polyclonal guinea pig anti-histidine decarboxylase, 1/2000 (from Euro-Diagnostica) and monoclonal mouse anti PCNA 1/2500 (Clone PC10 from Sigma). All antibodies were diluted in a 0.2% BSA solution. Sections were incubated overnight at 4° C. and then washed with a BSA solution.

secondary antibodies: goat anti guinea pig coupled to CY5, 1/500 (from Jackson Laboratories) and goat anti-mouse coupled to Cy3, 1/250 (from Jackson Laboratories); incubation for 4 hours at 37° C. After rinsing with BSA and PBS solutions, sections were mounted with slowfade (Molecular Probes Europe BV), and stored at 4° C.

Imaging

Fluorescence labelling was observed with an epifluorescence microscope or a Zeiss LSM510 (Carl Zeiss Jena GmbH) confocal microscope.

By using CY5- and CY3-coupled antibodies, the high autofluorescence properties of the oxyntic mucosa were circumvented when sections are illuminated by a 488 nm (FITC channel) light source. Negative controls, by omitting the primary antibodies, and an isotype control staining for PCNA showed complete absence of staining. The specific labelling of PCNA was checked using double staining with TOPRO-3® (Molecular Probes Europe BV), a nuclear stain. Only in the most luminal located epithelial cells, non-specific cytoplasmic labelling was present. In the glandular part of the mucosa, non-specific PCNA-staining was absent.

For determination of the labelling index of ECL cells, at least 80 confocal images per rat were taken from the 3 slides at the 3 different levels. The ratio of double labelled cells (HDC+PCNA) and all HDC labelled cells yielded the labelling index of ECL cells.

Proliferation activity of ECL cells in the PPI group is expected to be increased compared with sham, GRA and GRA-PPI groups (Eissele, R., Patberg, H., Koop, H., Krack, W., Lorenz, W., McKnight, A. T., and Arnold, R. Effect of gastrin receptor blockade on endrocine cells in rats during achlorhydria. *Gastroenterology*, 103, 1596–1601, 1992). Increased proliferation by PPI will be completely blocked by GRA.

What is claimed is:

1. A compound of the formula (I) or (II)

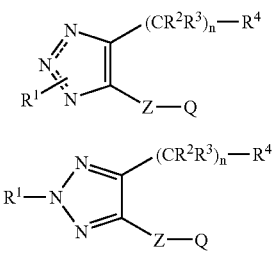

wherein n is from 1 to 4;

$R^1$ is H or $C_1$ to $C_{15}$ hydrocarbyl wherein up to three C atoms may optionally be replaced by an atom independently selected from the group consisting of N, O, and S, and up to three H atoms may optionally be replaced by halogen atoms;

$R^2$ is selected from the group consisting of H, Me, Et, Pr and OH, each $R^2$ being independently selected from the group consisting of H, Me, Et, Pr and OH when n is greater than 1;

$R^3$ is selected from the group consisting of H, Me, Et and Pr when n is 1; or, when n is greater than 1, each $R^3$ is independently selected from the group consisting of H, Me, Et and Pr, or two $R^3$ groups on neighbouring carbon atoms are linked to form a $C_3$ to $C_6$ carbocylic ring, or two $R^3$ groups are absent from neighbouring carbon atoms which are linked by a double bond;

$R^4$ is $C_1$ to $C_{15}$ hydrocarbyl wherein up to two C atoms may optionally be replaced by an atom independently selected from the group consisting of N, O, and S and up to three H atoms may optionally be replaced by halogen atoms;

Z is —CO—$(NR^6)$—, wherein $R^6$ is selected from the group consisting of H, Me, Et, Pr and Bn;

Q is

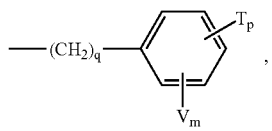

V is selected from the group consisting of —CO—NH—$SO_2$-Ph, —$SO_2$—NH—CO-Ph, —$CH_2OH$, and a group of the formula —$R^8U$, wherein U is selected from the group consisting of —COOH, tetrazolyl, —CONHOH— and —$SO_3H$; and $R^8$ is selected from the group consisting of a bond; $C_1$ to $C_6$ hydrocarbylene, optionally substituted by hydroxy, amino or acetamido; —O—($C_1$ to $C_3$ alkylene)-; —$SO_2NR^9$—$CHR^{19}$—; —CO—$NR^9$—$CHR^{10}$—, wherein $R^9$ and $R^{10}$ are in dependently selected from H and methyl; and —NH—$(CO)_c$—$CH_2$—, c being 0 or 1;

T is selected from the group consisting of $C_1$ to $C_6$ hydrocarbyl, —$NR^{11}R^{12}$ wherein $R^{11}$ and $R^{12}$ are independently selected from H, Me, Et, Pr, Bn, —OMe, —OH, —$CH_2OH$, halogen and trihalomethyl;

m is 1 or 2;

p is from 0 to 3; and q is from 0 to 2;

or a pharmaceutically acceptable salt thereof.

2. A compound according to any preceding claim wherein $R^1$ is $C_1$ to $C_{12}$ hydrocarbyl, wherein one C atom may optionally be replaced by N or O and up to three H atoms may optionally be replaced by F, Cl or Br.

3. A compound according to claim 1 wherein $R^1$ is selected from the group consisting of $C_3$ to $C_{12}$ alicyclic; phenyl optionally substituted with a moiety selected from the group consisting of OMe, $NMe_2$, $CF_3$, Me, F, Cl, Br and I; or $R^1$ is $C_1$ to $C_8$ alkyl.

4. A compound according to claim 1 wherein Z is CO—NH—.

5. A compound according to claim 1 wherein p is 0 or 1, and q is 0.

6. A compound according to claim 1 wherein T is $C_1$ to $C_6$ hydrocarbyl or halo.

7. A compound according to claim 1 wherein V is —$CO^2H$, —$CH_2CO^2H$ or tetrazolyl.

8. A compound according to claim 1 wherein $R^2$ and $R^3$ are H, and n is from 1 to 3.

9. A compound according to claim 8 wherein $R^4$ is $C_3$ to $C_{15}$ carbocyclic.

10. A compound according to claim 9 wherein $R^4$ is adamantyl, cyclopentyl, cyclohexy or phenyl.

11. A compound according to claim 8 wherein $R^4$ is NH—$R^{13}$ or —$OR^{13}$, in which $R^{13}$ is $C_3$ to $C_{12}$ carbocyclic.

12. A compound according to claim 11 wherein $R^{13}$ is adamantyl, cyclopentyl, cyclohexyl or phenyl.

13. A compound according to claim 1 wherein

V is —CO—NH—$SO_2$-Ph, —$SO_2$—NH—CO-Ph, —$OCH_2COOH$, tetrazolyl or —$(CH_2)_sCOOH$, wherein s is from 0 to 2; and T is $C_1$ to $C_6$ hydrocarbyl, —$NR^6R^7$, —OMe, —OH, —$CH_2OH$ or halogen, wherein wherein $R^7$ is —$CH_2$—; —$CH_2$—$CH_2$—; or

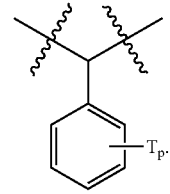

14. A compound which is degraded in vivo to yield a compound according to claim 1.

15. A method of making a compound according to claim 1 comprising the steps of (a) reacting a compound of formula (XVIII), or a suitably protected derivative thereof, with $R^1$—$NHNH_2$; and (b) cyclising the resultant product by activation of the hydroxyl group

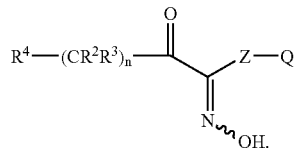

16. A method of making a compound according to claim 1 comprising the step of reacting a compound of formula (XIX), or a suitably protected derivative thereof, with a compound of formula $R^1N_3$

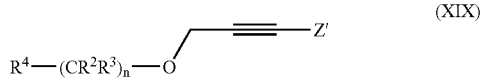 (XIX)

wherein Z' is a suitable precursor of the group ZQ.

17. A method according to claim 15 or 16 wherein $R^4$ is —O Adamantyl $R^2$ is H $R^3$ is H; and n is 1.

18. A pharmaceutical composition comprising a compound according to claim 1 together with a pharmaceutically acceptable diluent or carrier.

19. A pharmaceutical composition comprising a proton pump inhibitor and a compound according to claim 1 together with a pharmaceutically acceptable diluent or carrier.

20. A composition according to claim 19 wherein said proton pump inhibitor is selected from the group consisting of (RS)-rabeprazole, (RS)-omeprazole, lansoprazole, pantoprazole, (R)-omeprazole, (S)-omeprazole, perprazole, (R)-rabeprazole, (S)-rabeprazole, and the alkaline salts thereof.

21. A method of making a pharmaceutical composition comprising mixing a compound according to claim 1 with a pharmaceutically acceptable diluent or carrier.

22. A method of making a pharmaceutical composition, comprising mixing a compound according to claim 1 and a proton pump inhibitor with a pharmaceutically acceptable diluent or carrier.

23. A method of treating or alleviating the symptoms of a gastrointestinal disorder, comprising administering to a patient suffering from said disorder a therapeutically beneficial amount of a composition according to claim 19.

24. The method according to claim 23 wherein said composition provides a synergistic effect on said gastrointestinal disorder in said patient, and wherein said synergistic effect is reduction of acid secretion, prevention of a gastrointestinal disorder, or the reduction of one or more adverse effects associated with one of the active ingredients of said composition by the other active ingredients.

25. The method according to claim 23, wherein the amount of each of the active ingredients is equal to or less than that which is approved or indicated in monotherapy with said active ingredient.

26. A method of treating or alleviating the symptoms of a gastrointestinal disorder, comprising administering to a patient suffering from said disorder a therapeutically beneficial amount of a proton pump inhibitor and a compound according to claim 1, wherein said protein pump inhibitor and said compound are administered simultaneously, separately or sequentially.

27. A method of treating or alleviating the symptoms of a gastrointestinal disorder, comprising administering to a patient suffering from said disorder a therapeutically beneficial amount of a compound according to claim 1.

28. A method of treating or alleviating the symptoms of a gastrin-related disorder, comprising administering to a patient suffering from said disorder a therapeutically beneficial amount of a proton pump inhibitor and a compound according to claim 1, wherein said proton pump inhibitor enhances the effect of said compound.

29. The method according to claim 28, wherein said proton pump inhibitor and said compound are administered simultaneously or sequentially, and wherein said compound enhances the effect of said proton pump inhibitor on the reduction of acid secretion.

30. The method according to claim 28, wherein said proton pump inhibitor and said compound are administered simultaneously or sequentially, and wherein said compound reduces an adverse effect associated with administration of proton pump inhibitors.

31. The method according to claim 30, wherein said adverse effect is hyperplasia.

* * * * *